(12) United States Patent
Bur et al.

(10) Patent No.: US 8,846,733 B2
(45) Date of Patent: *Sep. 30, 2014

(54) OXAZOLYL-METHYLETHER DERIVATIVES AS ALX RECEPTOR AGONISTS

(75) Inventors: Daniel Bur, Allschwil (CH); Olivier Corminboeuf, Allschwil (CH); Sylvaine Cren, Allschwil (CH); Corinna Grisostomi, Allschwil (CH); Xavier Leroy, Allschwil (CH); Sylvia Richard-Bildstein, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/992,143

(22) PCT Filed: Dec. 6, 2011

(86) PCT No.: PCT/IB2011/055487
§ 371 (c)(1),
(2), (4) Date: Jun. 6, 2013

(87) PCT Pub. No.: WO2012/077049
PCT Pub. Date: Jun. 14, 2012

(65) Prior Publication Data
US 2013/0261159 A1 Oct. 3, 2013

(30) Foreign Application Priority Data
Dec. 7, 2010 (WO) .................. PCT/IB2010/055616

(51) Int. Cl.
*C07D 413/14* (2006.01)

(52) U.S. Cl.
CPC .................................. *C07D 413/14* (2013.01)
USPC ......................................... 514/374; 548/236

(58) Field of Classification Search
None
See application file for complete search history.

(56) References Cited

U.S. PATENT DOCUMENTS

| 8,288,419 | B2 | 10/2012 | Bur et al. |
| 2004/0043904 | A1 | 3/2004 | Yamaguchi et al. |
| 2010/0331378 | A1 | 12/2010 | Bur et al. |
| 2012/0115841 | A1 | 5/2012 | Bur et al. |
| 2012/0115916 | A1 | 5/2012 | Bur et al. |

FOREIGN PATENT DOCUMENTS

| JP | 62-234018 | 10/1987 |
| WO | WO 03/082314 | 10/2003 |
| WO | WO 2005/047899 | 5/2005 |
| WO | WO 2007/055941 | 5/2007 |
| WO | WO 2009/025793 | 2/2009 |
| WO | WO 2009/077954 | 6/2009 |
| WO | WO 2009/077990 | 6/2009 |
| WO | WO 2010/134014 | 11/2010 |
| WO | WO 2010/143116 | 12/2010 |
| WO | WO 2010/143158 | 12/2010 |

OTHER PUBLICATIONS

Das, U.N. Journal of Inflammation Research, 2010:3, pp. 143-170.*
Ninds, Creutzfeld-Jakob Disease Information Page, <www.ninds.nih.gov/disorders/cjd/cjd.htm> Accessed Aug. 11, 2012.*
"Alzheimer's disease." CNN Health, Obtained Oct. 9, 2010, URL:http://www.cnn.com/2003/HEALTH/conditions/09/24/alzheimers.drug.ap/index.html.*
Antonio R. Damasio, Alzheimer's Disease and Related Dementias, Cecil Textbook of Medicine, 20th edition (1996), vol. 2, pp. 1992-1996.*
Montine et al., The American Journal of Pathology, vol. 166, Issue 5 , pp. 1283-1289, May 2005.*
Yazawa Hiroshi et al., "β Amyloid Peptide ($AB_{42}$) is Internalized via the G-Protein-Coupled Receptor FPRL1 and Forms Fibrillar Aggregates in Macrophages" FASEB J., (2001), 15, pp. 2454-2462.
Burli, R. W. et al., "Potent hFPRL2 (ALXR) Agonists as Potential Anti-Inflammatory Agents" Bioorganic & Medicinal Chemistry Letters (2006), 16, p. 3713-3718.
Chiang N. et al., "The Lipoxin Receptor ALX: Potent Ligand-Specific and Stereoselective Actions in Vivo" Pharmacol. Rev. (2006), 58, No. 3, pp. 463-487.
Eagles T. E et al., "Some Nitro-1,2,3-Triazoles" Organic Preparations and Procedures (1970), 2(2), pp. 117-119.
Gould, Philip, "Salt selection for basic drugs," International Journal of Pharmaceuticals, (1986) 33, pp. 201-217.
Hermitage, S. et al., "A Efficient, Practical Approach to the Synthesis of 2,4-Disubstituted Thiazoles and Oxazoles: Application to the Synthesis of GW475151" Organic Process Research (2001), 5, pp. 37-44.
Le, Y. et al., "Biologically Active Peptides Interacting with the G Protein-Coupled Formylpeptide Receptors" Protein & Peptide Letters. (2007), 14, pp. 846-853.
Mallamo et al., "Antiandrogenic Steroidal Sulfonyl Heterocyles. Utility of Electrostatic Complementarity in Defining Bioisosteric Sulfonyl Heterocycles"; Journal of Medicinal Chemistry, vol. 35, No. 10, 1992, pp. 1663-1670.
Obushak, N. D. et al.; "Heterocyclic syntheses on the basis of arylation products of unsaturated compounds: X.*3-Aryl-2-chloropropanals as reagents for the synthesis of 2-amino-1,3-thiazole derivatives;" Russian Journal of Organic Chemistry, Consultants Bureau, US LNKD-DOI: 10.123/B:RUJO.0000034976.75646.85, vol. 40, No. 3, pp. 383-389; XP009097222; ISSN: 1070-4280; Jan. 1, 2004.

(Continued)

Primary Examiner — Alicia L Otton
(74) Attorney, Agent, or Firm — Hunton & Williams LLP

(57) ABSTRACT

The invention relates to oxazolyl-methylether derivatives of formula (I), (I)

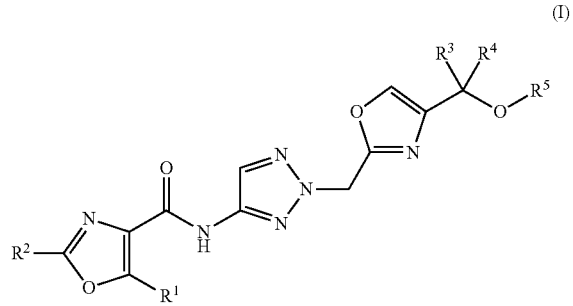

wherein $R^1$, $R^2$, $R^3$, $R^4$ and $R^5$ are as defined in the description, their preparation and their use as pharmaceutically active compounds.

17 Claims, No Drawings

(56) References Cited

OTHER PUBLICATIONS

Newman, P., "Nitro Derivatives of Phenyl-1,2,3-triazole (1)", Heterocycles Chem (1971) 8, pp. 51-56.
Remington: The Science and Practice of Pharmacy, 21st Edition, Lippincott, Williams and Wilkins Publishing, The University of the Sciences in Philadelphia, 2005.
Schwab, Jan M. et al., "Lipoxins and New Lipid Mediators in the Resolution of Inflammation" Current Opinion in Pharmacology (2006), pp. 414-420.
Wermuth C. G., "Molecular Variations Based on Isosteric Replacements" The Practice of Medicinal Chemistry (1996), pp. 203-237.
Yazawa Hiroshi et al., "β Amyloid Peptide ($AB_{42}$) is Internalized via the G-Protein-Coupled Receptor FPRL1 and Forms Fibrillar Aggregates in Macrophages" Bioorg. & Med. Chem Let. (2011), 11, pp. 6608-6612.
Ying, Guoguang et al., "Humanin, a Newly identified Neuroprotective Factor, Uses the G Protein-Coupled Formylpeptide Receptor-Like-1 as a Functional Receptor", J. Immunology (2004), 172, pp. 7078-7085.
U.S. Appl. No. 12/809,545, Non Final Office Action mailed from the USPTO on Aug. 14, 2012, 24 pages.
International Search Report of PCT/IB2011/055487, mailed Jul. 2, 2012.
Mamiya, Takayoshi et al., "[$Gly^{14}$]-Humanin improved the learning and memory impairment induced by scopolamine in vivo" British Journal of Pharmacology (2001) 134:1597-1599.
Miao, Jianting et al., "S14G-Humanin ameliorates Aβ25-35-induced behavioral deficits by reducing neuroinflammatory responses and apoptosis in mice" Neuropeptides (2008) 42(5-6):557-567.
Ying, Guoguang et al., "Humanin, a Newly Identified Neuroprotective Factor, Uses the G Protein-Coupled Formylpeptide Receptor-Like-1 as a Functional Receptor" The Journal of Immunology (2004) 172:7078-7085.

* cited by examiner

OXAZOLYL-METHYLETHER DERIVATIVES AS ALX RECEPTOR AGONISTS

CROSS-REFERENCE TO RELATED APPLICATIONS

This application is the U.S. National Phase of International Application No. of PCT/IB2011/055487, filed Dec. 6, 2011, which claims priority to PCT/IB2010/055616, filed Dec. 7, 2010, the contents of each are hereby incorporated by reference in their entireties.

The present invention relates to oxazolyl-methylether derivatives of formula (I) and their use as pharmaceuticals. The invention also concerns related aspects including processes for the preparation of the compounds, pharmaceutical compositions containing one or more compounds of formula (I), and especially their use as ALX receptor agonists.

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogs, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). ALXR was also identified as a functional receptor of a various number of peptides, including a fragment of the prion protein, a peptide derived from gp120 of the Human Immunodeficiency Virus (HIV)-1$_{LAI}$ strain, and amyloid-beta 1-42 (Ab42) (for review, Le et al., Protein Pepti Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. It was also reported that humanin (HN), a peptide with neuroprotective capabilities, shares the human ALXR with Ab42 on mononuclear phagocytes and neuronal cell lines and it has been suggested that the neuroprotective activity of HN may be attributed to its competitive occupation of ALXR (Ying et al., J. Immunol., 2004, 172, 7078-7085).

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

The present invention provides oxazolyl-methylether derivatives, which are non-peptide agonists of human ALX receptor. The compounds are useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

Other aminotriazole derivatives, which are also ALX receptor agonists, are disclosed in WO 2009/077990 and WO 2010/143116. Further ALX receptor agonists are disclosed in WO 2009/077954 and WO 2010/143158.

In contrast to compounds disclosed in WO 2009/077990 the kind of the heteroaryl group attached to the alkoxy-alkylether moiety has a surprisingly high influence on the agonistic activity of the presently claimed compounds. Additionally, the compounds of the present invention are more stable when tested in a plasma stability assay potentially leading to a lower covalent binding in the presence of plasma.

Various embodiments of the invention are presented hereafter:

1) The present invention relates to oxazolyl-methylether derivatives of formula (I),

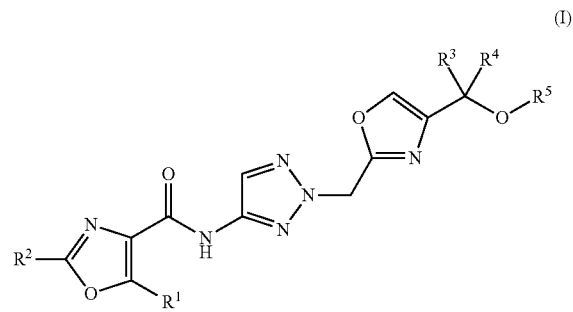

(I)

wherein
$R^1$ represents phenyl which is unsubstituted or mono-substituted with halogen, $(C_1-C_4)$alkyl, $(C_1-C_4)$alkoxy, $(C_1-C_2)$fluoroalkyl or $(C_1-C_2)$fluoroalkoxy;
$R^2$ represents hydrogen, methyl or cyclopropyl (and preferably hydrogen or methyl);
$R^3$ and $R^4$ are identical and represent hydrogen or methyl; and
$R^5$ represents $(C_1-C_2)$alkyl;
and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to four carbon atoms. The term "$(C_x-C_y)$alkyl" (x and y each being an integer), refers to an alkyl group as defined before containing x to y carbon atoms. For example a $(C_1-C_4)$alkyl group contains from one to four carbon atoms. Representative examples of alkyl groups include methyl, ethyl, n-propyl, iso-propyl, n-butyl, iso-butyl, sec-butyl and tert-butyl.

In case a $(C_1-C_4)$alkyl group is a substituent to a phenyl-group, the term "$(C_1-C_4)$alkyl" means $(C_1-C_4)$alkyl groups as defined above. Examples of said groups are methyl, ethyl, n-propyl, iso-propyl, n-butyl, iso-butyl, sec-butyl and tert-butyl. Preferred is methyl.

In case "$R^5$" represents "$(C_1-C_2)$alkyl" the term means $(C_1-C_2)$alkyl groups as defined above. Examples of said groups are methyl and ethyl. Preferred is methyl.

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. Preferred is methoxy.

The term "fluoroalkyl" refers to an alkyl group as defined before containing one or two carbon atoms in which one or more (and possibly all) hydrogen atoms have been replaced with fluorine. The term "$(C_x-C_y)$fluoroalkyl" (x and y each being an integer) refers to a fluoroalkyl group as defined before containing x to y carbon atoms. For example a $(C_1-C_2)$fluoroalkyl group contains one or two carbon atoms in which one to five hydrogen atoms have been replaced with fluorine. Representative examples of fluoroalkyl groups include difluoromethyl, trifluoromethyl and 2,2,2-trifluoroethyl. Preferred is $(C_1)$fluoroalkyl such as trifluoromethyl and difluoromethyl. Most preferred is trifluoromethyl.

The term "fluoroalkoxy" refers to an alkoxy group as defined before containing one or two carbon atoms in which one or more (and possibly all) hydrogen atoms have been replaced with fluorine. The term "$(C_x-C_y)$fluoroalkoxy" (x and y each being an integer) refers to a fluoroalkoxy group as defined before containing x to y carbon atoms. For example a $(C_1-C_2)$fluoroalkoxy group contains one or two carbon atoms in which one to five hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy. Most preferred is trifluoromethoxy.

The term halogen means fluoro, chloro, bromo or iodo, preferably fluoro, chloro or bromo and most preferably fluoro or chloro.

2) A further embodiment of the invention relates to oxazolyl-methylether derivatives according to embodiment 1), wherein
$R^1$ represents phenyl which is unsubstituted or mono-substituted with halogen, $(C_1-C_4)$alkyl, $(C_1-C_4)$alkoxy, $(C_1-C_2)$fluoroalkyl or $(C_1-C_2)$fluoroalkoxy;
$R^2$ represents hydrogen, methyl or cyclopropyl (and preferably hydrogen or methyl);
$R^3$ and $R^4$ are identical and represent hydrogen or methyl; and
$R^5$ represents methyl;
and to the salts (in particular pharmaceutically acceptable salts) of such compounds.

3) A further embodiment of the invention relates to oxazolyl-methylether derivatives according to embodiment 1), wherein
$R^1$ represents phenyl which is unsubstituted or mono-substituted with fluoro, chloro, methyl, methoxy, trifluoromethyl or trifluoromethoxy (and preferably unsubstituted or mono-substituted with fluoro, chloro, methyl or trifluoromethyl);
$R^2$ represents hydrogen or methyl (and preferably methyl);
$R^3$ and $R^4$ are identical and represent hydrogen or methyl; and
$R^5$ represents methyl;
and to the salts (in particular pharmaceutically acceptable salts) of such compounds.

4) A further embodiment of the invention relates to oxazolyl-methylether derivatives according to any one of embodiments 1) to 3), wherein
$R^1$ represents phenyl which is unsubstituted or mono-substituted with fluoro, chloro, methyl, methoxy, trifluoromethyl or trifluoromethoxy;
and to the salts (in particular pharmaceutically acceptable salts) of such compounds.

5) A further embodiment of the invention relates to oxazolyl-methylether derivatives according to any one of embodiments 1) to 3), wherein
$R^1$ represents phenyl which is unsubstituted or mono-substituted with halogen or $(C_1-C_4)$alkyl (and preferably unsubstituted or mono-substituted with fluoro, chloro or methyl);
and to the salts (in particular pharmaceutically acceptable salts) of such compounds.

6) A further embodiment of the invention relates to oxazolyl-methylether derivatives according to any one of embodiments 1) to 3), wherein
$R^1$ represents phenyl which is unsubstituted or mono-substituted with $(C_1-C_4)$alkyl (and preferably mono-substituted with methyl);
and to the salts (in particular pharmaceutically acceptable salts) of such compounds.

7) A further embodiment of the invention relates to oxazolyl-methylether derivatives according to any one of embodiments 1) to 6), wherein,
in case $R^1$ represents a mono-substituted phenyl group, said phenyl group is substituted in meta-position;
and to the salts (in particular pharmaceutically acceptable salts) of such compounds.

8) A further embodiment of the invention relates to oxazolyl-methylether derivatives according to any one of embodiments 1) to 7), wherein,
$R^2$ represents hydrogen or methyl;
and to the salts (in particular pharmaceutically acceptable salts) of such compounds.

9) A further embodiment of the invention relates to oxazolyl-methylether derivatives according to any one of embodiments 1) to 7), wherein,
$R^2$ represents hydrogen;
and to the salts (in particular pharmaceutically acceptable salts) of such compounds.

10) A further embodiment of the invention relates to oxazolyl-methylether derivatives according to any one of embodiments 1) to 7), wherein,
$R^2$ represents methyl;
and to the salts (in particular pharmaceutically acceptable salts) of such compounds.

11) A further embodiment of the invention relates to oxazolyl-methylether derivatives according to any one of embodiments 1) to 10), wherein, $R^3$ and $R^4$ both represent hydrogen;
and to the salts (in particular pharmaceutically acceptable salts) of such compounds.

12) A further embodiment of the invention relates to oxazolyl-methylether derivatives according to any one of embodiments 1) to 10), wherein,
$R^3$ and $R^4$ both represent methyl;
and to the salts (in particular pharmaceutically acceptable salts) of such compounds.

13) A further embodiment of the invention relates to oxazolyl-methylether derivatives according to any one of embodiments 1) to 12), wherein,
$R^5$ represents methyl;
and to the salts (in particular pharmaceutically acceptable salts) of such compounds.

14) Preferred compounds of formula (I) as defined in embodiment 1) are selected from the group consisting of:
N-(2-((4-(2-methoxypropan-2-yl)oxazol-2-yl)methyl)-2H-1,2,3-triazol-4-yl)-2-methyl-5-(m-tolyl)oxazole-4-carboxamide;
N-(2-((4-(methoxymethyl)oxazol-2-yl)methyl)-2H-1,2,3-triazol-4-yl)-2-methyl-5-(m-tolyl)oxazole-4-carboxamide;
N-(2-((4-(methoxymethyl)oxazol-2-yl)methyl)-2H-1,2,3-triazol-4-yl)-2-methyl-5-phenyloxazole-4-carboxamide;
5-(3-chlorophenyl)-N-(2-((4-(methoxymethyl)oxazol-2-yl)methyl)-2H-1,2,3-triazol-4-yl)-2-methyloxazole-4-carboxamide;
N-(2-((4-(methoxymethyl)oxazol-2-yl)methyl)-2H-1,2,3-triazol-4-yl)-2-methyl-5-(3-(trifluoromethyl)phenyl)oxazole-4-carboxamide;
5-(3-chlorophenyl)-N-(2-((4-(methoxymethyl)oxazol-2-yl)methyl)-2H-1,2,3-triazol-4-yl)oxazole-4-carboxamide;
N-(2-((4-(methoxymethyl)oxazol-2-yl)methyl)-2H-1,2,3-triazol-4-yl)-5-(3-methoxyphenyl)oxazole-4-carboxamide;
N-(2-((4-(methoxymethyl)oxazol-2-yl)methyl)-2H-1,2,3-triazol-4-yl)-5-(3-methoxyphenyl)-2-methyloxazole-4-carboxamide;
5-(3-fluorophenyl)-N-(2-((4-(methoxymethyl)oxazol-2-yl)methyl)-2H-1,2,3-triazol-4-yl)-2-methyloxazole-4-carboxamide;
N-(2-((4-(methoxymethyl)oxazol-2-yl)methyl)-2H-1,2,3-triazol-4-yl)-5-(m-tolyl)oxazole-4-carboxamide;
N-(2-((4-(methoxymethyl)oxazol-2-yl)methyl)-2H-1,2,3-triazol-4-yl)-2-methyl-5-(3-(trifluoromethoxy)phenyl)oxazole-4-carboxamide;
2-cyclopropyl-N-(2-((4-(methoxymethyl)oxazol-2-yl)methyl)-2H-1,2,3-triazol-4-yl)-5-(m-tolyl)oxazole-4-carboxamide; and
N-(2-((4-(methoxymethyl)oxazol-2-yl)methyl)-2H-1,2,3-triazol-4-yl)-5-phenyloxazole-4-carboxamide;
or salts (in particular pharmaceutically acceptable salts) of such compounds.

15) Further preferred compounds of formula (I) as defined in embodiment 1) are selected from the group consisting of:
N-(2-((4-(ethoxymethyl)oxazol-2-yl)methyl)-2H-1,2,3-triazol-4-yl)-2-methyl-5-(m-tolyl)oxazole-4-carboxamide; and
N-(2-((4-(ethoxymethyl)oxazol-2-yl)methyl)-2H-1,2,3-triazol-4-yl)-5-phenyloxazole-4-carboxamide;
or salts (in particular pharmaceutically acceptable salts) of such compounds.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 15), or pharmaceutically acceptable salts thereof, are suitable for use as medicaments. In particular, compounds of formula (I) modulate the ALX receptor, i.e. they act as ALX receptor agonists, and are useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the modulation of immune responses (especially those elicited by vaccination). Especially, compounds of formula (I) are useful for the prevention or treatment of diseases such as inflammatory diseases, obstructive airway diseases, allergic conditions, cardiovascular disorders, neuroinflammation, neurological disorders, pain, prion-mediated diseases and amyloid-mediated disorders (especially Alzheimer's disease).

In particular, the compounds of formula (I) according to any one of embodiments 1) to 15), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis, and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, controlled asthma, uncontrolled asthma, mild asthma, moderate asthma, severe asthma, bronchitis asthma, exercise-induced asthma, occupational asthma and induced asthma following bacterial infection.

5) In a further embodiment the compounds of formula (I) according to any one of embodiments 1) to 15), or pharmaceutically acceptable salts thereof, are particularly suitable for the prevention or treatment of inflammatory diseases. Inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.

5c) Further inflammatory diseases also relate to diseases or conditions having an inflammatory component. Diseases or conditions having an inflammatory component include, but are not limited to, diseases and conditions affecting the eye such as uveitis (anterior, intermediate and posterior), Behçet syndrome uveitis, conjunctivitis, keratoconjunctivitis sicca, Sjögren syndrome keratoconjunctivitis sicca, and vernal conjunctivitis (and especially conjunctivitis, keratoconjunctivitis sicca, and vernal conjunctivitis); diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behçet syndrome, Sjögren syndrome, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine ophthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis (and especially systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine ophthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis).

5d) Further inflammatory diseases in which autoimmune reactions are implicated or which have an autoimmune component or aetiology include rheumatoid arthritis, Hashimoto's thyroid and diabetes type I or II.

Further, the compounds of formula (I) according to any one of embodiments 1) to 15), or pharmaceutically acceptable salts thereof, are suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e g pancreatic islet cells.

Further, the compounds of formula (I) according to any one of embodiments 1) to 15), or pharmaceutically acceptable salts thereof, are suitable for the prevention or treatment of HIV-mediated retroviral infections.

HIV-mediated retroviral infections include, but are not limited to, one, several or all of the groups of diseases and disorders caused by HIV-1 and HIV-2 strains such as GUN-4-v, GUN-7 wt, AG204, AG206, AG208, HCM305, HCM308, HCM342, mSTD104, and HCM309.

Further, the compounds of formula (I) according to any one of embodiments 1) to 15), or pharmaceutically acceptable salts thereof, are suitable for the prevention or treatment of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 15), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to any one of embodiments 1) to 15), or pharmaceutically acceptable salts thereof, are suitable for the prevention or treatment of neurological disorders.

In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, Huntington's chorea, spinal muscular atrophy, polyglutamine diseases (such as spinobulbar muscular atrophy (Kennedy disease), spinocerebellar ataxia Type 1, 2, 3 (Machado-Joseph disease), 6, 7, 17) and cerebral malaria (and especially epilepsy, stroke, cerebral ischemia, cerebral palsy, relapsing remitting multiple sclerosis, progressive multiple sclerosis, Alpers' disease, amyotrophic lateral sclerosis (ALS), senile dementia, dementia with Lewy bodies, Rett syndrome, spinal cord trauma, traumatic brain injury, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea).

Further, the compounds of formula (I) according to any one of embodiments 1) to 15), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 15), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compounds of formula (I) according to any one of embodiments 1) to 15), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, vascular dementia, HIV-related dementia, Amyotrophic Lateral Sclerosis (ALS), inclusion-body myositis (IBM), Adult Onset Diabetes, and senile cardiac amyloidosis (and especially progressive supranuclear palsy, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis).

Further, the compounds of formula (I) according to any one of embodiments 1) to 15), or pharmaceutically acceptable salts thereof, are suitable for the modulation of immune responses.

The modulation of immune responses includes, but is not limited to, methods based on the administration to a subject a composition of at least one antigen and at least one compound of formula (I) according to any one of embodiments 1) to 15), or pharmaceutically acceptable salts thereof. In some cases, the antigen-containing composition is administrated first, followed by administration of a composition of at least one compounds of formula (I) according to any one of embodiments 1) to 15), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to any one of embodiments 1) to 15), or pharmaceutically acceptable salts thereof, and the antigen, as compared to sole administration of the antigen;

2) A greater sensitivity to small amounts of antigen (e.g., toxin or pathogen) or antigens that do not habitually induce strong immune responses; and 3) More effective anti-tumor therapies.

Further, the compounds of formula (I) according to any one of embodiments 1) to 15), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, or inflammatory diseases caused by pathogenic organisms.

Especially, compounds of formula (I) according to any one of embodiments 1) to 15), or pharmaceutically acceptable salts thereof, are suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, controlled asthma, uncontrolled asthma, mild asthma, moderate asthma, severe asthma, bronchitis asthma, exercise-induced asthma, occupational asthma and induced asthma following bacterial infection (and especially acute lung injury (ALI); adult/acute respiratory distress syndrome (ARDS); and asthma of whatever type or genesis, including intrinsic (non-allergic) asthma and extrinsic (allergic) asthma, controlled asthma, uncontrolled asthma, mild asthma, moderate asthma, severe asthma, bronchitis asthma, exercise-induced asthma, occupational asthma and induced asthma following bacterial infection);

2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;
3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);
4) HIV-mediated retroviral infections such as diseases and disorders caused by HIV-1 and HIV-2 strains such as GUN-4-v, GUN-7 wt, AG204, AG206, AG208, HCM305, HCM308, HCM342, mSTD104, and HCM309;
5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid β deposition of amyloid plaques;
6) Neurological disorders such as stroke, cerebral ischemia, Alzheimer's disease, and Parkinson's disease;
7) Prion-mediated diseases, also known as transmissible spongiform encephalopathies (TSEs), such as kuru, Gerstmann-Sträussler-Scheinker syndrome (GSS), Fatal Familial Insomnia (FFI) and Creutzfeldt-Jakob Disease (CJD);
8) Amyloid-mediated disorders;
9) Cystic fibrosis, wound healing and inflammatory diseases caused by pathogenic organisms.

The invention also relates to the use of a compound of formula (I) according to any one of embodiments 1) to 15) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 15).

A pharmaceutical composition according to the present invention contains at least one compound of formula (I) according to any one of embodiments 1) to 15) (or a pharmaceutically acceptable salt thereof) as the active agent and optionally carriers and/or diluents and/or adjuvants.

The compounds of formula (I) according to any one of embodiments 1) to 15) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 15), or a pharmaceutically acceptable salt thereof.

Any reference to a compound of formula (I) in this text is to be understood as referring also to the salts (and especially the pharmaceutically acceptable salts) of such compounds, as appropriate and expedient. The preferences indicated for the compounds of formula (I) of course apply mutatis mutandis to the salts and pharmaceutically acceptable salts of the compounds of formula (I). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, $R^4$ and $R^5$ are as defined for formula (I). Other abbreviations used are defined in the experimental section.

Reactions of alcohols with methanesulfonyl chloride (Ms-Cl) may result in the formation of the respective chloride or the respective mesylate derivative depending on the reaction conditions used; it is well known in the art that already small changes in such reaction conditions may have an influence on the outcome of said reactions; it should be understood that normally both reagents, the chloride and the mesylate, might be useful as electrophiles in reactions discussed below.

A. Synthesis of Final Products

A.a) The compounds of formula (I) can be prepared from amines of structure 1 by reaction with the appropriate carboxylic acid chloride at a temperature about rt in a suitable solvent such as $CH_2Cl_2$ in presence of a base such as $Et_3N$ or DIPEA. The appropriate carboxylic acid chloride can be prepared at a temperature about rt from the corresponding carboxylic acid of structure 5 by reaction with a reagent such as oxalyl chloride in presence of DMF in a suitable solvent such as toluene. Alternatively, amines of structure 1 can be coupled with the appropriate carboxylic acid of structure 5 using standard amide coupling conditions such as EDC/HOBt/

DMAP, or TBTU, or HBTU, or PyBOP in presence of a base such as DIPEA or Et₃N at a temperature about rt in a suitable solvent such as CH₂Cl₂ (or a mixture of CH₂Cl₂ and DMF) to give compounds of formula (I).

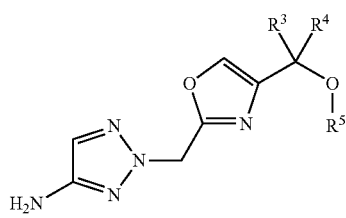

Structure 1

B. Synthesis of Intermediates

Compounds of structure 1 can be obtained from compounds of structure 2 by reduction of the nitro group either by hydrogenation in the presence of a metal catalyst such as Pd/C, Pt/C or PtO₂ at a temperature about rt in a suitable solvent such as MeOH or EtOH, or by reduction with a metal such as iron in a solvent mixture such as H₂O/EtOH in the presence of ammonium chloride at a temperature ranging from rt to about 95° C.

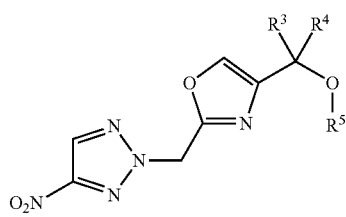

Structure 2

Compounds of structure 2 may be prepared by reacting compounds of structure 3 with 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) in the presence of a base such as K₂CO₃ or Cs₂CO₃ in a solvent such as acetone or AcCN at a temperature about rt or 80° C. (with or without addition of tetrabutylammonium bromide). Alternatively, the reaction may be performed in the presence of a base such as DIPEA in a solvent such as DMF, acetone or a mixture of both at a temperature about rt or 50° C.

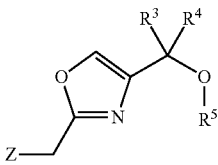

Z = Cl or MsO

Structure 3

Compounds of structure 3 may be prepared by alkylation of an alcohol of structure 4 with an alkyl iodide in presence of silver(I)-oxide (Ag₂O) in a solvent such as CH₂Cl₂.

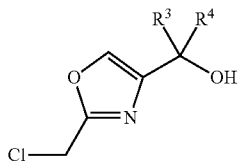

Structure 4

Compounds of structure 4 wherein R³ and R⁴ represent methyl may be prepared by addition of a methyl Grignard reagent to methyl 2-(chloromethyl)oxazole-4-carboxylate (Organic Process Research & Development 2001, 5, 37-44) at a temperature below rt (preferably about −78° C.) in a solvent such as THF, or, alternatively, by addition of a trimethylaluminum reagent at a temperature about 0° C. in a solvent such as CH₂Cl₂.

Compounds of structure 4 wherein R³ and R⁴ represent hydrogen may be prepared by reduction of methyl 2-(chloromethyl)oxazole-4-carboxylate using diisobutylaluminum hydride or LiAlH₄ at a temperature around 0° C. in a solvent such as THF.

Acids of structure 5 are commercially available, well known in the art or prepared according to the methods described in WO 2009/077990 (pages 112 to 116) or in analogy.

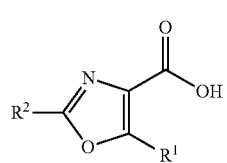

Structure 5

EXPERIMENTAL PART

Abbreviations (as Used Herein and in the Description Above)
Ac acetyl
AcCN acetonitrile
AlMe₃ trimethyl aluminium
aq. aqueous
COAD chronic obstructive airway disease
COLD chronic obstructive lung disease
COPD chronic obstructive pulmonary disease
DAD diode array detector
DCC N,N'-dicyclohexylcarbodiimide
dcm decays per minute
DIPEA diisopropylethylamine
DiBAL-H di-iso-butylaluminum hydride
DMAP 4-N,N-dimethylaminopyridine
DMEM dulbecco's modified eagle's medium
DMF dimethylformamide
DMSO dimethylsulfoxide
EA ethyl acetate
EC₅₀ half maximal effective concentration
EDC N-(3-dimethylaminopropyl)-N'-ethyl-carbodiimide hydrochloride
ELSD evaporative light-scattering detection
eq. equivalent(s)
Et ethyl
Ether or Et₂O diethylether
Et₃N triethylamine
EtOH ethanol FC flash column chromatography on silica gel
FLIPR fluorescence imaging plate reader
FPRL1 formyl-peptide receptor like-1
GSH glutathione
h hour(s)
HBTU O-(benzotriazol-1-yl)-N,N,N',N'-tetramethyluronium hexafluorophosphate
(Hank's) BSS (hanks') balanced salt solution
hept heptane
HIV human immunodeficiency virus
HLM human liver microsomes
HOBt hydroxybenzotriazole
HPLC high performance liquid chromatography
IU international units
LC-MS liquid chromatography-mass spectrometry
lem emission wavelength
lex excitation wavelength
Me methyl
MeOH methanol
min minute(s)
mM millimolar
μM micromolar
MS mass spectrometry
Ms methanesulfonyl
NADPH nicotinamide adenine dinucleotide phosphate
nm nanometer
nM nanomolar
NMR nuclear magnetic resonance
org. organic
p para
PG protecting group
PTFE polytetrafluoroethylene
PyBOP benzotriazol-1-yl-oxy-tris-pyrrolidino-phosphonium-hexafluoro-phosphate
Rochelle's salt potassium sodium tartrate
RCP radiochemical purity
rf retention factor
rpm rotation per minute
rt room temperature
sat. saturated
SDS sodium dodecyl sulfate
sol. solution
TBAF tetra-n-butylammonium fluoride
TBDMS tert-butyl-dimethyl-silyl
TBTU O-(benzotriazol-1-yl)-N,N,N',N'-tetramethyluronium tetrafluoroborate
TFA trifluoroacetic acid
THF tetrahydrofuran
TLC thin layer chromatography
$t_R$ retention time
UV ultra violet
Vis visible
I Chemistry
General.

All temperatures are stated in degrees Celsius (° C.). Unless otherwise indicated, the reactions take place at rt.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm); elution with EA, hept, $CH_2Cl_2$, $CHCl_3$, MeOH, $NH_4OH$ or mixtures thereof.

LC-MS-conditions 10 (if not indicated otherwise): Analytical: Dionex HPG-3000 Binary Pump, MS: Thermo MSQ MS, DAD: Dionex PDA 3000, ELSD: PolymerLab ELS 2100. Column: Ascentis Express C18 2.7 μm, 2.1×30 mm ID from Sigma-Aldrich, thermostated in the Dionex TCC-3000 compartment. Eluents: A: $H_2O$+0.05% $NH_4OH$+2% AcCN; B: AcCN. Method: Gradient: 5% B→95% B over 2.00 min. Flow: 1.8 mL/min. Detection: UV/Vis and/or ELSD, and MS, $t_R$ is given in min.

LC-MS-conditions 02 (if not indicated otherwise): Analytical: Thermo Finnigan MSQ Plus MS with Agilent 1100 Binary Pump and DAD. Column: Zorbax SB-AQ 5 μm, 4.6×50 mm ID from Agilent Technologies. Eluents: A: $H_2O$+0.04% TFA; B: AcCN; Gradient: 5% B→95% B over 1 min. Flow: 4.50 mL/min. Detection: UV/Vis and/or ELSD, and MS, $t_R$ is given in min.

LC-MS-conditions 04 (if not indicated otherwise): Analytical: Dionex P680, MS: Thermo MSQ Plus, DAD: Agilent G1315A, ELSD: Sedere Sedex 85. Column: Waters XBridge C18 5 μm, 4.6×50 mm. Eluents: A: water/NH3 ([NH3]=13 mmol); B: AcCN. Method: Gradient: 5% B→95% B over 0.75 min. Flow: 4.5 mL/min. Detection: UV/Vis and/or ELSD, and MS, $t_R$ is given in min.

LC-MS-conditions 06 (if not indicated otherwise): Analytical. Pump: Dionex HPG-3200RS, MS: Thermo MSQ Plus, DAD: Dionex DAD-3000RS, ELSD: Sedere Sedex 85. Column: Atlantis T3 5 μM, 4.6×30 mm ID from Waters, thermostated (40° C.) in the Dionex TCC-3200 compartment. Eluents: A: $H_2O$+0.04% TFA; B: AcCN. Method: Gradient: 5% B→95% B over 1.00 min. Flow: 4.5 mL/min. Detection: UV/Vis and/or ELSD, and MS, $t_R$ is given in min.

LC-MS-conditions 07 (if not indicated otherwise): Analytical: Pump: Dionex HPG-3200RS MS: Thermo Finnigan MSQ Plus, DAD: Dionex DAD-3000RS, ELSD: Sedere Sedex 85. Column: Zorbax SB-AQ 3.5 μm, 4.6×50 mm ID from Agilent Technologies, thermostated (40° C.) in the Dionex TCC-3200 compartment. Eluents: A: $H_2O$+0.04% TFA; B: AcCN; Gradient: 5% B→95% B over 1 min. Flow: 4.50 mL/min. Detection: UV/Vis and/or ELSD, and MS, $t_R$ is given in min.

HPLC preparative: X-Bridge C18 5 μm, 50×19 mm ID from Waters. Eluents: A: $H_2O$+0.5% $NH_4OH$; B: AcCN; Gradient: 10% B→90% B over 5 min. Flow: 40.0 mL/min. Detection: UV/Vis and/or ELSD, and MS, $t_R$ is given in min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

General Procedures
General Procedure 1 (GP1): Amide Coupling:

In a vial equipped with a magnetic stir bar and under an inert atmosphere ($N_2$), the desired acid (1.5 eq) was treated sequentially with a) 2-((4-(methoxymethyl)oxazol-2-yl)methyl)-2H-1,2,3-triazol-4-amine (0.1 mmol, 1.0 eq.) 0.4M in a 4 to 1 mixture of $CH_2Cl_2$/DMF (0.25 mL), b) a mixture of HOBT (2.0 eq.), DMAP (0.25 eq.) and DIPEA (2.0 eq) in $CH_2Cl_2$ (0.25 mL) and c) EDC (1.5 eq) in $CH_2Cl_2$ (0.5 mL). The reaction mixture was then stirred until completion at rt. The resulting solution was loaded into a syringe containing diatomaceous earth from International Sorbent Technology (isolute HM-N) (800 mg) conditioned with water (0.6 mL)

and the syringe was washed with $CH_2Cl_2$ (5×1 mL). The solvent was removed under reduced pressure. Purification by preparative HPLC afforded the desired material.

Synthesis of Reference Compounds

Reference Compound 1

N-(2-((2-(Methoxymethyl)thiazol-5-yl)methyl)-2H-1,2,3-triazol-4-yl)-2-methyl-5-(m-tolyl)oxazole-4-carboxamide In a flame dried round-bottomed flask equipped with a magnetic stir bar and under inert atmosphere ($N_2$), a solution of 2-methyl-5-(m-tolyl)oxazole-4-carboxylic acid (WO 2009/077990, p. 112) (70.0 mg, 0.32 mmol) in $CH_2Cl_2$ (1.5 mL) was treated at rt with DMAP (9.8 mg, 0.08 mmol), HOBt (52 mg, 0.39 mmol), EDC (154 mg, 0.81 mmol) and DIPEA (0.22 mL, 1.3 mmol) and the resulting mixture was stirred for 30 min at rt. A solution of 2-((2-(methoxymethyl)thiazol-5-yl)methyl)-2H-1,2,3-triazol-4-amine (73 mg, 0.32 mmol) in $CH_2Cl_2$ (1.5 mL) was then added and the reaction mixture was stirred overnight at rt. The mixture was diluted with $CH_2Cl_2$ (5.0 mL), the layers were separated and the org. phase was washed with water (5.0 mL) dried over $Na_2SO_4$, filtered and the solvents were removed under reduced pressure. Purification of the residue by FC (4:6 hept-EA) gave the title compound as a colorless oil: TLC: rf (4:6 hept-EA)=0.29. LC-MS-conditions 07: $t_R$=0.94 min, $[M+H]^+$=425.09.

Reference Compound 2

N-(2-((5-(Methoxymethyl)thiazol-2-yl)methyl)-2H-1,2,3-triazol-4-yl)-2-methyl-5-(m-tolyl)oxazole-4-carboxamide In a flame dried round-bottomed flask equipped with a magnetic stir bar and under inert atmosphere ($N_2$), a solution of 2-methyl-5-(m-tolyl)oxazole-4-carboxylic acid (WO 2009/077990, p. 112) (61.0 mg, 0.28 mmol) in $CH_2Cl_2$ (1.5 mL) was treated at rt with DMAP (8.5 mg, 0.07 mmol), HOBt (45.6 mg, 0.34 mmol), EDC (135 mg, 0.70 mmol) and DIPEA (0.19 mL, 1.12 mmol) and the resulting mixture was stirred for 30 min at rt. A solution of 2-((5-(methoxymethyl)thiazol-2-yl)methyl)-2H-1,2,3-triazol-4-amine (63 mg, 0.28 mmol) in $CH_2Cl_2$ (1.5 mL) was then added and the reaction mixture was stirred overnight at rt. The mixture was diluted with $CH_2Cl_2$ (5.0 mL), the layers were separated and the org. phase was washed with water (5.0 mL) dried over $Na_2SO_4$, filtered and the solvents were removed under reduced pressure. Purification of the residue by FC (4:6 hept-EA) gave the title compound as a colorless oil: TLC: rf (4:6 hept-EA)=0.29. LC-MS-conditions 07: $t_R$=0.92 min, $[M+H]^+$=425.09.

Reference Compound 3

N-(2-((5-(methoxymethyl)furan-2-yl)methyl)-2H-1,2,3-triazol-4-yl)-5-phenyloxazole-4-carboxamide In a flame dried round-bottomed flask equipped with a magnetic stir bar and under inert atmosphere ($N_2$), a solution of commercially available 5-phenyloxazole-4-carboxylic acid (52 mg, 0.26 mmol) in $CH_2Cl_2$ (3.0 mL) was treated at rt with DMAP (8.1 mg, 0.07 mmol), HOBt (42.8 mg, 0.32 mmol), EDC (127 mg, 0.66 mmol) and DIPEA (0.2 mL, 1.17 mmol) and the resulting mixture was stirred for 30 min at rt. A solution of 2-((5-(methoxymethyl)furan-2-yl)methyl)-2H-1,2,3-triazol-4-amine (55 mg, 0.26 mmol) in $CH_2Cl_2$ (3.0 mL) was then added and the reaction mixture was stirred overnight at rt. The mixture was diluted with $CH_2Cl_2$ (10.0 mL), the layers were separated and the org. phase was washed with water (10.0 mL), followed by brine (10.0 mL) and dried over $MgSO_4$, filtered and the solvents were removed under reduced pressure. Purification of the residue by FC (6:4 hept-EA) gave the title compound as a colorless oil: TLC: rf (6:4 hept-EA)=0.23. LC-MS-conditions 07: $t_R$=0.87 min, $[M+H]^+$=380.26

Reference Compound 4

N-(2-((5-(methoxymethyl)thiophen-2-yl)methyl)-2H-1,2,3-triazol-4-yl)-5-phenyloxazole-4-carboxamide In a flame dried round-bottomed flask equipped with a magnetic stir bar and under inert atmosphere ($N_2$), a solution of commercially available 5-phenyloxazole-4-carboxylic acid (120 mg, 0.62 mmol) in $CH_2Cl_2$ (4.0 mL) was treated at rt with DMAP (19 mg, 0.15 mmol), HOBt (103 mg, 0.74 mmol), EDC (301 mg, 1.54 mmol) and DIPEA (0.5 mL, 2.77 mmol) and the resulting mixture was stirred for 15 min at rt. A solution of 2-((5-(methoxymethyl)thiophen-2-yl)methyl)-2H-1,2,3-triazol-4-amine (131 mg, 0.61 mmol) in $CH_2Cl_2$ (8.0 mL) was then added and the reaction mixture was stirred overnight at rt. The mixture was diluted with $CH_2Cl_2$ (15.0 mL), the layers were separated and the org. phase was washed with 1N HCl (15.0 mL), water (15.0 mL), followed by brine (15.0 mL) and dried over $MgSO_4$, filtered and the solvents were removed under reduced pressure. Purification of the residue by FC (gradient from 85:15 hept-EA to 70:30 hept-EA) gave the title compound as a white solid. TLC: rf (7:3 hept-EA)=0.2. LC-MS-conditions 07: $t_R$=0.90 min, $[M+H]^+$=396.03

Reference Compound 5

N-(2-((4-(methoxymethyl)thiazol-2-yl)methyl)-2H-1,2,3-triazol-4-yl)-5-phenyloxazole-4-carboxamide In a flame dried round-bottomed flask equipped with a magnetic stir bar and under inert atmosphere ($N_2$), a solution of commercially available 5-phenyloxazole-4-carboxylic acid (64 mg, 0.33 mmol) in $CH_2Cl_2$ (3.0 mL) was treated at rt with DMAP (10 mg, 0.08 mmol), HOBt (55 mg, 0.39 mmol), EDC (157 mg, 0.82 mmol) and DIPEA (0.25 mL, 1.48 mmol) and the resulting mixture was stirred for 15 min at rt. A solution of 2-((4-(methoxymethyl)thiazol-2-yl)methyl)-2H-1,2,3-triazol-4-amine (74 mg, 0.33 mmol) in $CH_2Cl_2$ (3.5 mL) was then added and the reaction mixture was stirred overnight at rt. The mixture was diluted with $CH_2Cl_2$ (15.0 mL), the layers were separated and the org. phase was washed with 1N HCl (15.0 mL), water (10.0 mL), followed by brine (10.0 mL) and dried over $MgSO_4$, filtered and the solvents were removed under reduced pressure. Purification of the residue by FC (gradient from 90:10 hept-EA to 60:40 hept-EA) gave the title compound as a white solid. TLC: rf (7:3 hept-EA)=0.15. LC-MS-conditions 07: $t_R$=0.83 min, $[M+H]^+$=397.21

Reference Compound 6

N-(2-((2-(methoxymethyl)thiazol-4-yl)methyl)-2H-1,2,3-triazol-4-yl)-5-phenyloxazole-4-carboxamide In a flame dried round-bottomed flask equipped with a magnetic stir bar and under inert atmosphere ($N_2$), a solution of commercially available 5-phenyloxazole-4-carboxylic acid (42 mg, 0.21 mmol) in CH$_2$Cl$_2$ (3.0 mL) was treated at rt with DMAP (6.6 mg, 0.05 mmol), HOBt (36 mg, 0.26 mmol), EDC (102 mg, 0.53 mmol) and DIPEA (0.16 mL, 0.96 mmol) and the resulting mixture was stirred for 45 min at rt. A solution of 2-((2-(methoxymethyl)thiazol-4-yl)methyl)-2H-1,2,3-triazol-4-amine (48 mg, 0.21 mmol) in CH$_2$Cl$_2$ (3.0 mL) was then added and the reaction mixture was stirred overnight at rt. The mixture was diluted with CH$_2$Cl$_2$ (15.0 mL), the layers were separated and the org. phase was washed with 1N HCl (10.0 mL), water (5.0 mL), followed by brine (10.0 mL) and dried over MgSO$_4$, filtered and the solvents were removed under reduced pressure. Purification of the residue by FC (60:40 hept-EA) gave the title compound as a white solid. TLC: rf (7:3 hept-EA)=0.15. LC-MS-conditions 07: t$_R$=0.83 min, [M+H]$^+$=397.23.

Reference Compound 7

N-(2-((2-(methoxymethyl)thiazol-5-yl)methyl)-2H-1,2,3-triazol-4-yl)-5-phenyloxazole-4-carboxamide In a flame dried round-bottomed flask equipped with a magnetic stir bar and under inert atmosphere (N$_2$), a solution of commercially available 5-phenyloxazole-4-carboxylic acid (30.0 mg, 0.16 mmol) in CH$_2$Cl$_2$ (1.0 mL) was treated at rt with DMAP (4.8 mg, 0.04 mmol), HOBt (26 mg, 0.19 mmol), EDC (76 mg, 0.40 mmol) and DIPEA (0.11 mL, 0.63 mmol) and the resulting mixture was stirred for 30 min at rt. A solution of 2-((2-(methoxymethyl)thiazol-5-yl)methyl)-2H-1,2,3-triazol-4-amine (36 mg, 0.16 mmol) in CH$_2$Cl$_2$ (0.6 mL) was then added and the reaction mixture was stirred overnight at rt. The solvents were removed under reduced pressure. Purification of the residue by HPLC gave the title compound as a beige solid. TLC: rf (4:6 hept-EA)=0.30. LC-MS-conditions 07: t$_R$=0.87 min, [M+H]$^+$=397.39.

Reference Compound 8

N-(2-((5-(methoxymethyl)thiazol-2-yl)methyl)-2H-1,2,3-triazol-4-yl)-5-phenyloxazole-4-carboxamide In a flame dried round-bottomed flask equipped with a magnetic stir bar and under inert atmosphere (N$_2$), a solution of commercially available 5-phenyloxazole-4-carboxylic acid (30 mg, 0.16 mmol) in CH$_2$Cl$_2$ (1.0 mL) was treated at rt with DMAP (4.8 mg, 0.04 mmol), HOBt (26 mg, 0.19 mmol), EDC (76 mg, 0.40 mmol) and DIPEA (0.11 mL, 0.63 mmol) and the resulting mixture was stirred for 30 min at rt. A solution of 2-((5-(methoxymethyl)thiazol-2-yl)methyl)-2H-1,2,3-triazol-4-amine (36 mg, 0.16 mmol) in CH$_2$Cl$_2$ (0.6 mL) was then added and the reaction mixture was stirred overnight at rt. The solvents were removed under reduced pressure. Purification of the residue by preparative HPLC gave the title compound as a yellow oil. TLC: rf (4:6 hept-EA)=0.31. LC-MS-conditions 07: t$_R$=0.85 min, [M+H]$^+$=397.40.

Reference Compound 9

N-(2-((2-(2-methoxypropan-2-yl)oxazol-4-yl)methyl)-2H-1,2,3-triazol-4-yl)-5-phenyloxazole-4-carboxamide In a flame dried round-bottomed flask equipped with a magnetic stir bar and under inert atmosphere (N$_2$), a solution of commercially available 5-phenyloxazole-4-carboxylic acid (18 mg, 0.10 mmol) in CH$_2$Cl$_2$ (1.0 mL) was treated at rt with DMAP (3.0 mg, 0.02 mmol), HOBt (15.7 mg, 0.12 mmol), EDC (46.5 mg, 0.24 mmol) and DIPEA (0.07 mL, 0.39 mmol) and the resulting mixture was stirred for 45 min at rt. A solution of 2-((2-(2-methoxypropan-2-yl)oxazol-4-yl)methyl)-2H-1,2,3-triazol-4-amine (23.0 mg, 0.10 mmol) in CH$_2$Cl$_2$ (0.5 mL) was then added and the reaction mixture was stirred overnight at rt. The mixture was diluted with CH$_2$Cl$_2$ (10.0 mL), the layers were separated and the org. phase was washed with water (5.0 mL), dried over MgSO$_4$, filtered and the solvents were removed under reduced pressure. Purification of the residue by FC (50:50 hept-EA) gave the title compound as a yellow oil. TLC: rf (50:50 hept-EA)= 0.27. LC-MS-conditions 07: t$_R$=0.86 min, [M+H]$^+$=408.89.

Reference Compound 10

N-(2-((2-(Methoxymethyl)oxazol-4-yl)methyl)-2H-1,2,3-triazol-4-yl)-2-methyl-5-(m-tolyl)oxazole-4-carboxamide In a flame dried round-bottomed flask equipped with a magnetic stir bar and under inert atmosphere (N$_2$), a solution of 2-methyl-5-(m-tolyl)oxazole-4-carboxylic acid (WO 2009/077990, p. 112) (14 mg, 0.06 mmol) in CH$_2$Cl$_2$ (0.3 mL) was treated at rt with DMAP (2 mg, 0.02 mmol), HOBt (10 mg, 0.08 mmol), EDC (31 mg, 0.16 mmol) and DIPEA (0.04 mL, 0.26 mmol) and the resulting mixture was stirred for 45 min at rt. A solution of 2-((2-(methoxymethyl)oxazol-4-yl)methyl)-2H-1,2,3-triazol-4-amine (13 mg, 0.06 mmol) in CH$_2$Cl$_2$ (0.3 mL) was then added and the reaction mixture was stirred overnight at rt. The mixture was diluted with CH$_2$Cl$_2$ (5 mL), the org. phase was washed with water (5 mL), dried over Na$_2$SO$_4$, filtered and the solvents were removed under reduced pressure. Purification of the residue by FC (1:2 hept-EA) gave the title compound as a colorless oil: TLC: rf (1:2 hept-EA)=0.36. LC-MS-conditions 07: t$_R$=0.88 min, [M+H]$^+$=408.69.

Reference Compound 11

N-(2-((4-acetyloxazol-2-yl)methyl)-2H-1,2,3-triazol-4-yl)-2-methyl-5-(m-tolyl)oxazole-4-carboxamide In a flame dried round-bottomed flask equipped with a magnetic stir bar and under inert atmosphere (N$_2$), a solution of 2-methyl-5-(m-tolyl)oxazole-4-carboxylic acid (WO 2009/077990, p. 112) (590 mg, 2.72 mmol) in CH$_2$Cl$_2$ (20 mL) was treated at rt with DMAP (82 mg, 0.68 mmol), HOBt (441 mg, 3.62 mmol), EDC (1.3 g, 6.79 mmol) and DIPEA (1.8 mL, 10.86 mmol) and the resulting mixture was stirred for 30 min at rt. A solution of 1-(2-((4-amino-2H-1,2,3-triazol-2-yl)methyl)oxazol-4-yl)ethanone (WO 2009/077990, p. 105) (562 mg, 2.72 mmol) in CH$_2$Cl$_2$ (7.0 mL) was then added and the reaction mixture was stirred overnight at rt. The mixture was diluted with CH$_2$Cl$_2$ (50 mL), the org. phase was washed with water (50 mL), dried over MgSO$_4$, filtered and the solvents were removed under reduced pressure. Purification of the residue by FC (4:6 hept-EA) gave the title compound as a white solid: TLC: rf (4:6 hept-EA)=0.35. LC-MS-conditions 07: t$_R$=0.88 min, [M+H]$^+$=407.05.

Synthesis of Intermediates 2-((5-(Methoxymethyl)furan-2-yl)methyl)-4-nitro-2H-1,2,3-triazole In a flame dried round-bottomed flask equipped with a magnetic stir bar and under inert atmosphere (N$_2$), a solution of (5-((4-nitro-2H-1,2,3-triazol-2-yl)methyl)furan-2-yl) methanol (WO 2009077990A1) (186 mg, 0.83 mmol) in CH$_2$Cl$_2$ (3.0 mL) was added to a suspension of Ag$_2$O (288 mg, 1.24 mmol) and MeI (0.06 mL, 0.99 mmol). The resulting mixture (protected form light) was stirred overnight at 40° C. The reaction mixture was filtered and the solvent was removed under reduced pressure. Purification of the residue by FC (7:3 hept-EA) gave the title compound as a yellow oil: TLC: rf (7:3 hept-EA)=0.27. LC-MS-conditions 07: $t_R$=0.74 min.

2-((5-(Methoxymethyl)furan-2-yl)methyl)-2H-1,2,3-triazol-4-amine

In a flame dried round-bottomed flask equipped with a magnetic stir bar and under inert atmosphere (N$_2$), a mixture of 2-((5-(methoxymethyl)furan-2-yl)methyl)-4-nitro-2H-1,2,3-triazole (97 mg, 0.35 mmol), iron powder (59 mg, 1.04 mmol) and NH$_4$Cl (94 mg, 1.74 mmol) in a mixture of EtOH (1.6 mL) and water (0.8 mL) was stirred at 90° C. for 2 h. The reaction mixture was filtered while hot and concentrated under reduced pressure. CH$_2$Cl$_2$ (20 mL) was added followed by 1N NaOH (10 mL). The layers were separated and the aq. layer was extracted with CH$_2$Cl$_2$ (10 mL). The combined org. extracts were dried over Na$_2$SO$_4$, filtered, and the solvents were removed under reduced pressure. Purification of the residue by FC (95:5 CH$_2$Cl$_2$-MeOH) gave the title compound as a yellow oil: TLC: rf (95:5 CH$_2$Cl$_2$-MeOH)=0.39. LC-MS-conditions 07: $t_R$=0.51 min, [M+H]$^+$=209.34.

2-(Methoxymethyl)thiophene

In a flame dried round-bottomed flask equipped with a magnetic stir bar and under inert atmosphere (N$_2$), a solution of commercially available thiophen-2-ylmethanol (1.46 g, 12.8 mmol) in CH$_2$Cl$_2$ (7.5 mL) was treated with MeI (3.0 mL, 48.2 mmol) followed by Ag$_2$O (4.44 g, 19.1 mmol) and the resulting mixture (protected form light) was stirred overnight at 40° C. The reaction mixture was filtered and the solvent was removed under reduced pressure. Purification of the residue by FC (95:5 hept-EA) gave the title compound as a yellow oil. LC-MS-conditions 07: $t_R$=0.67.

5-(Methoxymethyl)thiophene-2-carbaldehyde

In a flame dried round-bottomed flask equipped with a magnetic stir bar and under inert atmosphere (N$_2$), a solution of 2-(methoxymethyl)thiophene (1.23 g, 9.58 mmol) in THF (50.0 mL) was treated dropwise at −75° C. with N,N,N',N'-tetramethyl-ethylendiamin (2.69 ml, 17.7 mmol) followed by n-BuLi (6.5 mL of a 2.7 M solution in heptane, 17.7 mmol). The resulting mixture was stirred for 90 min at −70° C. DMF (4.03 mL, 52.1 mmol) was then added and the resulting mixture was allowed to gently warm-up to rt. The mixture was then poured over sat. aq. NH$_4$Cl (40 mL) and the org. layer was extracted with EA (3×20 mL) and the combined org. layers were dried over MgSO$_4$, filtered and the solvent was removed under reduced pressure. Purification of the residue by FC (gradient from 95:5 hept-EA to 85:15 hept-EA) gave the title compound as an orange oil. LC-MS-conditions 07: $t_R$=0.62 min.

(5-(Methoxymethyl)thiophen-2-yl)methanol

In a flame dried round-bottomed flask equipped with a magnetic stir bar and under inert atmosphere (N$_2$), a solution of 5-(methoxymethyl)thiophene-2-carbaldehyde (782 mg, 5.01 mmol) in EtOH (10 mL) was treated at 0° C. with NaBH$_4$ (379 mg, 10.0 mmol) and the resulting solution was stirred for 5 min at 0° C. and then allowed to warm to rt. Water (5 mL) and EA (5 mL) were added. The aq. layer was extracted with EA (2×15 mL) and the combined org. layers were washed with brine, dried over MgSO$_4$, filtered and the solvent was removed under reduced pressure to give the title compound as a yellow oil. LC-MS-conditions 07: $t_R$=0.51 min.

2-((5-(Methoxymethyl)thiophen-2-yl)methyl)-4-nitro-2H-1,2,3-triazole

In a flame dried round-bottomed flask equipped with a magnetic stir bar and under inert atmosphere (N$_2$), a solution of (5-(methoxymethyl)thiophen-2-yl)methanol (900 mg, 5.69 mmol) in dry CH$_2$Cl$_2$ (20.0 mL) was treated at 0° C. with Et$_3$N (1.19 mL, 8.53 mmol) followed by DMAP (70 mg, 0.57 mmol) and Ms-Cl (0.57 mL, 7.39 mmol). After stirring at 0° C. for 1 h, the reaction was quenched with water (5 mL). The layers were separated and the aq. layer was extracted with CH$_2$Cl$_2$ (2×10 mL). The combined org. extracts were dried over MgSO$_4$, filtered, and the solvents were removed under reduced pressure to give 1.38 of crude (5-(methoxymethyl) thiophen-2-yl)methyl methanesulfonate as an orange oil. LC-MS-conditions 07: $t_R$=0.51 min. A solution of this crude material in DMF (10.0 mL) was added to a solution of 4-nitro-2H-[1,2,3]triazole (7.05 g of a 9.6% solution in DMF, 5.93 mmol) in DMF (15.0 mL) pre-treated for 30 min with DIPEA (1.96 mL, 11.9 mmol) and the reaction mixture was stirred overnight at 50° C. Water (10 mL), followed by EA (10 mL) was added. The aq. layer was extracted with EA (2×15 mL) and the combined org. extracts were washed with brine, dried over MgSO$_4$, filtered, and the solvents were removed under reduced pressure. Purification of the residue by FC (gradient from 95:5 hept-EA to 80:20 hept-EA) gave the title compound as a yellow oil. TLC: rf (8:2 hept-EA)=0.36. LC-MS-conditions 07: $t_R$=0.80 min.

2-((5-(Methoxymethyl)thiophen-2-yl)methyl)-2H-1,2,3-triazol-4-amine

In a flame dried round-bottomed flask equipped with a magnetic stir bar and under inert atmosphere (N$_2$), a mixture of 2-((5-(methoxymethyl)thiophen-2-yl)methyl)-4-nitro-2H-1,2,3-triazole (169 mg, 0.67 mmol), iron powder (131 mg, 2.33 mmol) and NH$_4$Cl (215 mg, 3.99 mmol) in a mixture of EtOH (4.6 mL) and water (2.4 mL) was stirred at 50° C. for 30 min. The reaction mixture was filtered while hot and concentrated under reduced pressure. CH$_2$Cl$_2$ (20 mL) was added followed by 3N NaOH (5 mL). The layers were separated and the aq. layer was extracted with CH$_2$Cl$_2$ (3×15 mL). The combined org. extracts were dried over MgSO$_4$, filtered, and the solvents were removed under reduced pressure to give the title compound as a yellow oil. LC-MS-conditions 07: $t_R$=0.58 min, [M+H]$^+$=225.18.

Methyl 2-((4-nitro-2H-1,2,3-triazol-2-yl)methyl) thiazole-4-carboxylate

In a flame dried round-bottomed flask equipped with a magnetic stir bar and under inert atmosphere (N$_2$), a solution of methyl 2-(chloromethyl)thiazole-4-carboxylate (S. A. Hermitage et al. *Organic Process Research & Development*, 5, 37-44, 2001) (2.05 g, 10.7 mmol) in DMF (20.0 mL) was added to a solution of 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971)

(11.53 g of a 8% solution in DMF, 9.70 mmol) in DMF (20.0 mL) pre-treated for 30 min with DIPEA (3.21 mL, 19.4 mmol) and the reaction mixture was stirred overnight at 50° C. Water (50 mL), followed by EA (50 mL) was added. The layers were separated and the aq. layer was extracted with EA (2×50 mL), dried over MgSO$_4$, filtered, and the solvents were removed under reduced pressure. Purification of the residue by FC (gradient from 60:40 hept-EA to 50:50 hept-EA)) gave the title compound as a yellow solid. TLC: rf (6:4 hept-EA)= 0.31. LC-MS-conditions 07: $t_R$=0.67 min, [M+H]$^+$=270.21.

(2-((4-Nitro-2H-1,2,3-triazol-2-yl)methyl)thiazol-4-yl)methanol

In a flame dried round-bottomed flask equipped with a magnetic stir bar and under inert atmosphere (N$_2$), a solution of methyl 2-((4-nitro-2H-1,2,3-triazol-2-yl)methyl)thiazole-4-carboxylate (1.10 g, 4.08 mmol) in THF (30 mL) was treated dropwise at 0° C. with DiBAL-H (14.3 mL of a 1.0 M solution in THF, 14.3 mmol) and the resulting solution was stirred for 1 h at 0°. Rochelle's salt solution (100 mL) was added and the mixture was stirred for 1 h at rt. The aq. layer was extracted with EA (2×40 mL) and the combined org. layers were dried over MgSO$_4$, filtered and the solvent was removed under reduced pressure to give the title compound as a yellow oil. LC-MS-conditions 07: $t_R$=0.53 min; [M+H]$^+$= 241.95.

4-(Methoxymethyl)-2-((4-nitro-2H-1,2,3-triazol-2-yl)methyl)thiazole

In a flame dried round-bottomed flask equipped with a magnetic stir bar and under inert atmosphere (N$_2$), a solution of (2-((4-nitro-2H-1,2,3-triazol-2-yl)methyl)thiazol-4-yl)methanol (672 mg, 2.79 mmol) in CH$_2$Cl$_2$ (15.0 mL) was added to a suspension of Ag$_2$O (968 mg, 4.18 mmol) and MeI (0.52 mL, 8.36 mmol). The resulting mixture (protected form light) was stirred overnight at 40° C. The reaction mixture was filtered and the solvent was removed under reduced pressure. Purification of the residue by FC (6:4 hept-EA) gave the title compound as a yellow oil. LC-MS-conditions 07: $t_R$=0.66 min, [M+H]$^+$=226.27.

2-((4-(Methoxymethyl)thiazol-2-yl)methyl)-2H-1,2,3-triazol-4-amine

In a flame dried round-bottomed flask equipped with a magnetic stir bar and under inert atmosphere (N$_2$), a mixture of 4-(methoxymethyl)-2-((4-nitro-2H-1,2,3-triazol-2-yl)methyl)thiazole (85 mg, 0.31 mmol), iron powder (66 mg, 1.17 mmol) and NH$_4$Cl (108 mg, 2.0 mmol) in a mixture of EtOH (2.0 mL) and water (1.0 mL) was stirred at 75° C. for 25 min. The reaction mixture was filtered while hot and concentrated under reduced pressure. CH$_2$Cl$_2$ (15 mL) was added followed by 1N NaOH (10 mL). The layers were separated and the aq. layer was extracted with CH$_2$Cl$_2$ (3×10 mL). The combined org. extracts were dried over MgSO$_4$, filtered, and the solvents were removed under reduced pressure to give the title compound as a yellow oil. LC-MS-conditions 07: $t_R$=0.47 min, [M+H]$^+$=226.30.

Ethyl 4-((4-nitro-2H-1,2,3-triazol-2-yl)methyl)thiazole-2-carboxylate

In a flame dried round-bottomed flask equipped with a magnetic stir bar and under inert atmosphere (N$_2$), a solution of ethyl 4-(chloromethyl)thiazole-2-carboxylate (WO 2009077990 A1) (2.16 g, 10.5 mmol) in DMF (15.0 mL) was added to a solution of 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) (8.0 g of a 10% solution in DMF, 7.01 mmol) in DMF (15.0 mL) pre-treated for 30 min with DIPEA (1.82 mL, 2.33 mmol) and the reaction mixture was stirred overnight at 50° C. Water (50 mL), followed by EA (50 mL) was added. The layers were separated and the aq. layer was washed with water (50 mL), dried over MgSO$_4$, filtered, and the solvents were removed under reduced pressure. Purification of the residue by FC (60:40 hept-EA)) gave the title compound as a yellow oil. TLC: rf (7:3 hept-EA)=0.36. LC-MS-conditions 07: $t_R$=0.76 min, [M+H]$^+$=284.28.

(4-((4-Nitro-2H-1,2,3-triazol-2-yl)methyl)thiazol-2-yl)methanol

In a flame dried round-bottomed flask equipped with a magnetic stir bar and under inert atmosphere (N$_2$), a solution of ethyl 4-((4-nitro-2H-1,2,3-triazol-2-yl)methyl)thiazole-2-carboxylate (845 mg, 2.98 mmol) in THF (30 mL) was treated dropwise at 0° C. with DiBAL-H (11.3 mL of a 1.0 M solution in toluene, 11.3 mmol) and the resulting solution was stirred for 1 h at 0°. Rochelle's salt solution (100 mL) was added and the mixture was stirred for 1 h at rt. The aq. layer was extracted with EA (2×40 mL) and the combined org. layers were dried over MgSO$_4$, filtered and the solvent was removed under reduced pressure. Purification of the residue by FC (40:60 hept-EA)) gave the title compound as a yellow oil. TLC: rf (4:6 hept-EA)=0.25. LC-MS-conditions 07: $t_R$=0.54 min, [M+H]$^+$=241.95.

2-(Methoxymethyl)-4-((4-nitro-2H-1,2,3-triazol-2-yl)methyl)thiazole

In a flame dried round-bottomed flask equipped with a magnetic stir bar and under inert atmosphere (N$_2$), a solution of (4-((4-nitro-2H-1,2,3-triazol-2-yl)methyl)thiazol-2-yl)methanol (419 mg, 1.74 mmol) in CH$_2$Cl$_2$ (15.0 mL) was added to a suspension of Ag$_2$O (604 mg, 2.61 mmol) and MeI (0.33 mL, 5.21 mmol). The resulting mixture (protected form light) was stirred overnight at 40° C. The reaction mixture was filtered and the solvent was removed under reduced pressure. Purification of the residue by FC (1:1 hept-EA) gave the title compound as a yellow oil. TLC: rf (1:1 hept-EA)=0.36. LC-MS-conditions 07: $t_R$=0.68 min, [M+H]$^+$=256.27.

2-((2-(Methoxymethyl)thiazol-4-yl)methyl)-2H-1,2,3-triazol-4-amine

In a flame dried round-bottomed flask equipped with a magnetic stir bar and under inert atmosphere (N$_2$), a mixture of 2-(methoxymethyl)-4-((4-nitro-2H-1,2,3-triazol-2-yl)methyl)thiazole (200 mg, 0.78 mmol), iron powder (133 mg, 2.35 mmol) and NH$_4$Cl (212 mg, 3.92 mmol) in a mixture of EtOH (10.0 mL) and water (5.0 mL) was stirred at 100° C. for 2 h. The reaction mixture was filtered while hot and concentrated under reduced pressure. CH$_2$Cl$_2$ (40 mL) was added followed by 1N NaOH (20 mL). The layers were separated and the aq. layer was extracted with CH$_2$Cl$_2$ (2×10 mL). The combined org. extracts were dried over MgSO$_4$, filtered, and the solvents were removed under reduced pressure to give the title compound which was purified by preparative HPLC to give a colorless oil. LC-MS-conditions 07: $t_R$=0.47 min, [M+H]$^+$=226.30.

(E)-(2-Styryloxazol-4-yl)methanol

In a flame dried round-bottomed flask equipped with a magnetic stir bar and under inert atmosphere ($N_2$), a solution of (E)-ethyl 2-styryloxazole-4-carboxylate (WO 2009077990 A1) (8.5 g, 34.9 mmol) in THF (28.3 mL) was treated dropwise at 0° C. with DiBAL-H (85.0 mL of a 1.0 M solution in toluene, 85.0 mmol) and the resulting solution was stirred for 1.5 h at 0° C. Rochelle's salt solution was added followed by EA and the mixture was stirred for 24 h at rt. The aq. layer was extracted with EA (3×40 mL) and the combined org. layers were dried over $Na_2SO_4$, filtered and the solvent was removed under reduced pressure to give the title compound as an orange oil. TLC: rf (1:1 hept-EA)=0.20. LC-MS-conditions 07: $t_R$=0.71 min, $[M+H]^+$=202.15.

(E)-4-(((tert-Butyldimethylsilyl)oxy)methyl)-2-styryloxazole

In a flame dried round-bottomed flask equipped with a magnetic stir bar and under inert atmosphere ($N_2$), a solution of (E)-(2-styryloxazol-4-yl)methanol (5.40 g, 26.8 mmol) in $CH_2Cl_2$ (56.0 mL) was treated at rt with tert-butylchlorodimethylsilane (8.52 g, 53.67 mmol) followed by imidazole (3.69 g, 53.67 mmol) and the resulting suspension was stirred for 1 h at rt. Water was added. The aq. layer was extracted with and the combined org. layers were dried over $Na_2SO_4$, filtered and the solvent was removed under reduced pressure. Purification of the residue by FC (gradient from hept to 9:1 hept-EA) gave the title compound as a yellow oil. TLC: rf (9:1 hept-EA)= 0.35. LC-MS-conditions 07: $t_R$=1.08 min, $[M+H]^+$=316.13.

4-(((tert-Butyldimethylsilyl)oxy)methyl)oxazole-2-carbaldehyde

In a flame dried round-bottomed flask equipped with a magnetic stir bar and under inert atmosphere ($N_2$), a solution of NaIO4 (726 mg, 3.33 mmol) in water (6.6) mL was slowly added to a vigorously stirred suspension of silica gel (4.46 g) in acetone (13.2 mL). The mixture was then concentrated under reduced pressure and the lumpy solid slurried in $CH_2Cl_2$ and the solvent was evaporated under reduced pressure. $CH_2Cl_2$ (16.5 mL) was added and the reaction mixture was treated at rt with (E)-4-(((tert-butyldimethylsilyl)oxy) methyl)-2-styryloxazole (350 mg, 1.1 mmol) and $RuCl_3$ hydrate (7.8 mg, 0.03 mmol). The reaction mixture was stirred at rt in the dark overnight, filtered through silica gel and concentrated under reduced pressure to give the title compound as a red oil. TLC: rf (1:3 EA-Hept)=0.51. LC-MS-conditions 07: $t_R$=0.64 min.

1-(4-(((tert-Butyldimethylsilyl)oxy)methyl)oxazol-2-yl)ethanol

In a flame dried round-bottomed flask equipped with a magnetic stir bar and under inert atmosphere ($N_2$), a solution of 4-(((tert-butyldimethylsilyl)oxy)methyl)oxazole-2-carbaldehyde (268 mg, 1.11 mmol) in $CH_2Cl_2$ (9.2 mL) was treated dropwise at 0° C. with trimethylaluminium (1.11 mL of a 2.0 M solution in toluene, 2.22 mmol) and the resulting yellow solution was stirred for 45 min at 0° C. Sat. aq. $NH_4Cl$ was added to the reaction mixture which was extracted with $CH_2Cl_2$ (3×25 mL) and the combined org. layers were dried over $Na_2SO_4$, filtered and the solvent was removed under reduced pressure. Purification of the residue by FC (1:1 hept-EA) gave the title compound as a yellow oil: TLC: rf (1:1 hept-EA)=0.40. LC-MS-conditions 07: $t_R$=0.85 min, $[M]^+$=257.81.

1-(4-(((tert-Butyldimethylsilyl)oxy)methyl)oxazol-2-yl)ethanone

In a flame dried round-bottomed flask equipped with a magnetic stir bar and under inert atmosphere ($N_2$), a solution of 1-(4-(((tert-butyldimethylsilyl)oxy)methyl)oxazol-2-yl) ethanol (260 mg, 1.01 mmol) in AcCN (7.1 mL) was treated at rt with $MnO_2$ (1488 mg, 5.05 mmol) and the resulting mixture was stirred overnight at rt. The reaction mixture was filtered and the solvent was removed under reduced pressure to give the title compound as a yellow oil. TLC: rf (2:1 hept-EA)=0.55. LC-MS-conditions 07: $t_R$=0.96 min, $[M]^+$=255.89.

2-(4-(((tert-Butyldimethylsilyl)oxy)methyl)oxazol-2-yl)propan-2-ol

In a flame dried round-bottomed flask equipped with a magnetic stir bar and under inert atmosphere ($N_2$), a solution of 1-(4-(((tert-butyldimethylsilyl)oxy)methyl)oxazol-2-yl) ethanone (171 mg, 0.67 mmol) in $CH_2Cl_2$ (5.6 mL) was treated dropwise at 0° C. with trimethylaluminium (0.56 mL of a 2.0 M solution in toluene, 1.12 mmol) and the resulting yellow solution was stirred for 90 min at 0° C. Sat. aq. $NH_4Cl$ was added to the reaction mixture which was extracted with $CH_2Cl_2$ (3×25 mL) and the combined org. layers were dried over $Na_2SO_4$, filtered and the solvent was removed under reduced pressure to give the title compound as a yellow oil. LC-MS-conditions 07: $t_R$=0.88 min, $[M+H]^+$=272.20.

4-(((tert-Butyldimethylsilyl)oxy)methyl)-2-(2-methoxypropan-2-yl)oxazole

In a flame dried round-bottomed flask equipped with a magnetic stir bar and under inert atmosphere ($N_2$), a solution of 2-(4-(((tert-butyldimethylsilyl)oxy)methyl)oxazol-2-yl) propan-2-ol (153 mg, 0.56 mmol) in $CH_2Cl_2$ (0.4 mL) was treated with MeI (0.08 mL, 1.35 mmol) followed by $Ag_2O$ (196 mg, 0.85 mmol). The resulting mixture (protected form light) was stirred overnight at 40° C. The reaction mixture was filtered and the solvent was removed under reduced pressure. Purification of the residue by FC (7:3 hept-EA) gave the title compound as an orange oil. TLC: rf (7:3 hept-EA)=0.40. LC-MS-conditions 07: $t_R$=0.99 min, $[M+H]^+$=286.20.

(2-(2-Methoxypropan-2-yl)oxazol-4-yl)methanol

In a flame dried round-bottomed flask equipped with a magnetic stir bar and under inert atmosphere ($N_2$), a solution of 4-(((tert-butyldimethylsilyl)oxy)methyl)-2-(2-methoxypropan-2-yl)oxazole (110 mg, 0.39 mmol) in THF (1.8 mL) was treated at 0° C. with TBAF (0.39 mL of a 1M solution in THF, 0.39 mmol) and the resulting mixture was stirred for 45 min at 0° C. The reaction mixture was diluted with EA (10 mL), washed with sat. aq. $NH_4Cl$ (5 mL) and brine, dried over $MgSO_4$, filtered and the solvent was removed under reduced pressure. Purification of the residue by FC (3:7 hept-EA) gave the title compound as a yellow oil: TLC: rf (3:7 hept-EA)= 0.20. LC-MS-conditions 07: $t_R$=0.44 min, $[M+H]^+$=172.01.

2-(2-Methoxypropan-2-yl)-4-((4-nitro-2H-1,2,3-triazol-2-yl)methyl)oxazole

In a flame dried round-bottomed flask equipped with a magnetic stir bar and under inert atmosphere ($N_2$), a solution of (2-(2-methoxypropan-2-yl)oxazol-4-yl)methanol (31 mg, 0.18 mmol) in dry $CH_2Cl_2$ (1.4 mL) was treated at 0° C. with $Et_3N$ (0.03 mL, 0.23 mmol) followed by DMAP (2.2 mg, 0.02 mmol) and Ms-Cl (0.02 mL, 0.23 mmol). After stirring at 0° C. for 30 min, the reaction was quenched with water (10 mL). The org. layer was dried over $Na_2SO_4$, filtered, and the solvents were removed under reduced pressure to give 44 mg of crude (2-(2-methoxypropan-2-yl)oxazol-4-yl)methyl methanesulfonate as a yellow oil. LC-MS-conditions 07: $t_R$=0.62 min, $[M+H]^+$=250.00. A solution of this crude material (44 mg) in DMF (0.4 mL) was added to a solution of 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) (203 mg of a 9.6% solution in DMF, 0.17 mmol) in DMF (0.4 mL) pre-treated for 30 min with DIPEA (0.06 mL, 0.34 mmol) and the reaction mixture was stirred for 24 h at 50° C. Water (5 mL), followed by EA (5 mL) was added. The aq. layer was extracted with EA (10 mL) and the combined org. extracts were dried over $MgSO_4$, filtered, and the solvents were removed under reduced pressure. Purification of the residue by FC (1:1 hept-EA) gave the title compound as a yellow oil: TLC: rf (1:1 hept-EA)=0.43. LC-MS-conditions 07: $t_R$=0.72 min, $[M]^+$=267.96.

2-((2-(2-Methoxypropan-2-yl)oxazol-4-yl)methyl)-2H-1,2,3-triazol-4-amine

In a flame dried round-bottomed flask equipped with a magnetic stir bar and under inert atmosphere ($N_2$), a mixture of 2-(2-methoxypropan-2-yl)-4-((4-nitro-2H-1,2,3-triazol-2-yl)methyl)oxazole (33 mg, 0.12 mmol), iron powder (21 mg, 0.37 mmol) and $NH_4Cl$ (33 mg, 0.62 mmol) in a mixture of EtOH (0.4 mL) and water (0.2 mL) was stirred at 85° C. for 30 min. The reaction mixture was filtered while hot and concentrated under reduced pressure. $CH_2Cl_2$ (5 mL) was added followed by 1N NaOH (5 mL). The layers were separated and the aq. layer was extracted with $CH_2Cl_2$ (5×5 mL). The combined org. extracts were dried over $Na_2SO_4$, filtered, and the solvents were removed under reduced pressure to give the title compound as an orange oil. LC-MS-conditions 07: $t_R$=0.51 min; $[M]^+$=237.17.

2-Bromo-5-(methoxymethyl)thiazole

In a flame dried round-bottomed flask equipped with a magnetic stir bar and under inert atmosphere ($N_2$), a solution of (2-bromothiazol-5-yl)methanol (WO 2009/077990, p. 92) (1.19 g, 6.11 mmol) in $CH_2Cl_2$ (4.0 mL) was treated with MeI (0.46 mL, 7.33 mmol) followed by $Ag_2O$ (2.12 g, 9.16 mmol) and the resulting mixture (protected form light) was stirred overnight at 40° C. The reaction mixture was filtered and the solvent was removed under reduced pressure. Purification of the residue by FC (7:3 hept-EA) gave the title compound as a colorless oil: TLC: rf (7:3 hept-EA)=0.33. LC-MS-conditions 07: $t_R$=0.66 min, $[M+H]^+$=209.93.

(5-(Methoxymethyl)thiazol-2-yl)methanol

In a flame dried round-bottomed flask equipped with a magnetic stir bar and under inert atmosphere ($N_2$), a solution of 2-bromo-5-(methoxymethyl)thiazole (944 mg, 4.54 mmol) in $Et_2O$ (10.0 mL) was treated dropwise at −70° C. with n-BuLi (2.98 mL of a 1.6M solution in hexane, 4.76 mmol). The resulting mixture was stirred for 30 min at −70° C. DMF (0.56 mL, 7.26 mmol) was then added and the resulting mixture was stirred for 20 min at −70° C.

Sat. aq. $NH_4Cl$ was added, the org. layer was extracted with EA (3×20 mL) and the combined org. layers were dried over $MgSO_4$, filtered and the solvent was removed under reduced pressure to give 543 mg of 5-(methoxymethyl)thiazole-2-carbaldehyde as a yellow oil: TLC: rf (9:1 hept-EA)=0.32. A solution of this material in MeOH (10 mL) was treated at 0° C. with $NaBH_4$ (169 mg, 4.29 mmol). After 15 min at 0° C., water followed by EA was added. The org. layer was extracted with EA (3×20 mL) and the combined org. layers were dried over $Na_2SO_4$, filtered and the solvent was removed under reduced pressure. Purification of the residue by FC (1:2 hept-EA) gave the title compound as a yellow oil: TLC: rf (1:2 hept-EA)=0.25. LC-MS-conditions 07: $t_R$=0.42 min, $[M+H]^+$= 160.17.

5-(Methoxymethyl)-2-((4-nitro-2H-1,2,3-triazol-2-yl)methyl)thiazole

In a flame dried round-bottomed flask equipped with a magnetic stir bar and under inert atmosphere ($N_2$), a solution of (5-(methoxymethyl)thiazol-2-yl)methanol (201 mg, 1.26 mmol) in dry $CH_2Cl_2$ (10.0 mL) was treated at 0° C. with $Et_3N$ (0.23 mL, 1.63 mmol) followed by DMAP (15.6 mg, 0.13 mmol) and Ms-Cl (0.13 mL, 1.59 mmol). After stirring at 0° C. for 30 min, the reaction was quenched with water (10 mL). The org. layer was dried over $Na_2SO_4$, filtered, and the solvents were removed under reduced pressure to give 300 mg of crude (5-(methoxymethyl)thiazol-2-yl)methyl methanesulfonate as an orange oil. LC-MS-conditions 07: $t_R$=0.59 min, $[M+H]^+$=238.07. A solution of this crude material (300 mg) in DMF (3.0 mL) was added to a solution of 4-nitro-2H-[1,2,3]triazole (1.50 g of a 9.6% solution in DMF, 1.26 mmol) in DMF (3.0 mL) pre-treated for 30 min with DIPEA (0.43 mL, 2.53 mmol) and the reaction mixture was stirred for 24 h at 50° C. Water (10 mL), followed by EA (10 mL) was added. The aq. layer was extracted with EA (10 mL) and the combined org. extracts were dried over $MgSO_4$, filtered, and the solvents were removed under reduced pressure. Purification of the residue by FC (1:1 hept-EA) gave the title compound as a yellow oil: TLC: rf (1:1 hept-EA)=0.29. LC-MS-conditions 07: $t_R$=0.70 min, $[M+H]^+$=255.85.

2-((5-(Methoxymethyl)thiazol-2-yl)methyl)-2H-1,2,3-triazol-4-amine

In a flame dried round-bottomed flask equipped with a magnetic stir bar and under inert atmosphere ($N_2$), a mixture of 5-(methoxymethyl)-2-((4-nitro-2H-1,2,3-triazol-2-yl)methyl)thiazole (80 mg, 0.31 mmol), iron powder (53 mg, 0.93 mmol) and $NH_4Cl$ (84 mg, 1.56 mmol) in a mixture of EtOH (1.0 mL) and water (0.5 mL) was stirred at 85° C. for 30 min. The reaction mixture was filtered while hot and concentrated under reduced pressure. $CH_2Cl_2$ (5 mL) was added followed by 1N NaOH (5 mL). The layers were separated and the aq. layer was extracted with $CH_2Cl_2$ (2×5 mL). The combined org. extracts were dried over $Na_2SO_4$, filtered, and the solvents were removed under reduced pressure to give the title compound as a yellow oil. LC-MS-conditions 07: $t_R$=0.49 min; $[M+H]^+$=226.17.

(5-(((tert-Butyldimethylsilyl)oxy)methyl)thiazol-2-yl)methanol

In a flame dried round-bottomed flask equipped with a magnetic stir bar and under inert atmosphere ($N_2$), a solution of 2-bromo-5-(((tert-butyldimethylsilyl)oxy)methyl)thiazole (WO 2009/077990, p. 92) (2.0 g, 6.49 mmol) in $Et_2O$ (14.0 mL) was treated dropwise at −70° C. with n-BuLi (4.25 mL of a 1.6M solution in hexane, 6.81 mmol). The resulting mixture was stirred for 30 min at −70° C. DMF (0.80 mL, 10.38 mmol) was then added and the resulting mixture was stirred for 20 min at −70° C. Sat. aq. NH$_4$Cl was added, the org. layer was extracted with EA (3×20 mL) and the combined org. layers were dried over MgSO$_4$, filtered and the solvent was removed under reduced pressure to give 1.50 g of 5-(((tert-butyldimethylsilyl)oxy)methyl)thiazole-2-carbaldehyde as a yellow oil: TLC: rf (9:1 hept-EA)=0.31. LC-MS-conditions 07: t$_R$=1.00 min, [M+H]$^+$=257.93. A solution of this material in MeOH (10 mL) was treated at 0° C. with NaBH$_4$ (286 mg, 7.25 mmol). After 30 min at 0° C., water followed by EA were added. The org. layer was extracted with EA (3×20 mL) and the combined org. layers were dried over Na$_2$SO$_4$, filtered and the solvent was removed under reduced pressure. Purification of the residue by FC (1:1 hept-EA) gave the title compound as a yellow oil: TLC: rf (1:1 hept-EA)=0.33. LC-MS-conditions 07: t$_R$=0.87 min, [M+H]$^+$=260.06.

5-(((tert-Butyldimethylsilyl)oxy)methyl)-2-(methoxymethyl)thiazole

In a flame dried round-bottomed flask equipped with a magnetic stir bar and under inert atmosphere (N$_2$), a solution of (5-(((tert-butyldimethylsilyl)oxy)methyl)thiazol-2-yl) methanol (1.21 g, 4.65 mmol) in CH$_2$Cl$_2$ (3.0 mL) was treated with MeI (0.35 mL, 5.57 mmol) followed by Ag$_2$O (1.61 g, 6.97 mmol) and the resulting mixture (protected from light) was stirred overnight at 40° C. The reaction mixture was filtered and the solvent was removed under reduced pressure. Purification of the residue by FC (4:1 hept-EA) gave the title compound as a yellow oil: TLC: rf (4:1 hept-EA)=0.27. LC-MS-conditions 07: t$_R$=0.99 min, [M+H]$^+$=273.95.

(2-(Methoxymethyl)thiazol-5-yl)methanol

In a flame dried round-bottomed flask equipped with a magnetic stir bar and under inert atmosphere (N$_2$), a solution of 5-(((tert-butyldimethylsilyl)oxy)methyl)-2-(methoxymethyl)thiazole (721 mg, 2.64 mmol) in THF (20 mL) was treated at 0° C. with TBAF (5.30 mL of a 1M solution in THF, 5.30 mmol) and the resulting mixture was stirred for 45 min at 0° C. The reaction mixture was diluted with EA, washed with sat. aq. NH$_4$Cl and brine, dried over Na$_2$SO$_4$, filtered and the solvent was removed under reduced pressure. Purification of the residue by FC (1:9 hept-EA) gave the title compound as a colorless oil: TLC: rf (1:9 hept-EA)=0.27. LC-MS-conditions 07: t$_R$=0.41 min, [M+H]$^+$=160.01.

2-(Methoxymethyl)-5-((4-nitro-2H-1,2,3-triazol-2-yl)methyl)thiazole

In a flame dried round-bottomed flask equipped with a magnetic stir bar and under inert atmosphere (N$_2$), a solution of (2-(methoxymethyl)thiazol-5-yl)methanol (319 mg, 2.00 mmol) in dry CH$_2$Cl$_2$ (15.0 mL) was treated at 0° C. with Et$_3$N (0.36 mL, 2.59 mmol) followed by DMAP (25 mg, 0.20 mmol) and Ms-Cl (0.20 mL, 2.53 mmol). After stirring at 0° C. for 30 min, the reaction was quenched with water (10 mL). The org. layer was dried over Na$_2$SO$_4$, filtered, and the solvents were removed under reduced pressure to give 469 mg (quant.) of crude (2-(methoxymethyl)thiazol-5-yl)methyl methanesulfonate as an yellow oil: TLC: rf (1:4 hept-EA)= 0.39. A solution of this crude material (469 mg) in DMF (4.5 mL) was added to a solution of 4-nitro-2H-[1,2,3]triazole (2.35 g of a 9.6% solution in DMF, 1.98 mmol) in DMF (4.5 mL) pre-treated for 30 min with DIPEA (0.68 mL, 3.96 mmol) and the reaction mixture was stirred for 4 days at 50° C. Water (10 mL), followed by EA (10 mL) were added. The aq. layer was extracted with EA (10 mL) and the combined org. extracts were dried over MgSO$_4$, filtered, and the solvents were removed under reduced pressure. Purification of the residue by FC (1:1 hept-EA) gave the title compound as a yellow oil: TLC: rf (1:1 hept-EA)=0.33. LC-MS-conditions 07: t$_R$=0.72 min, [M+H]$^+$=255.95.

2-((2-(methoxymethyl)thiazol-5-yl)methyl)-2H-1,2,3-triazol-4-amine

In a flame dried round-bottomed flask equipped with a magnetic stir bar and under inert atmosphere (N$_2$), a mixture of 2-(methoxymethyl)-5-((4-nitro-2H-1,2,3-triazol-2-yl)methyl)thiazole (109 mg, 0.43 mmol), iron powder (72 mg, 1.28 mmol) and NH$_4$Cl (115 mg, 2.14 mmol) in a mixture of EtOH (2.0 mL) and water (1.0 mL) was stirred at 85° C. for 15 min. The reaction mixture was filtered while hot and concentrated under reduced pressure. CH$_2$Cl$_2$ (5 mL) was added followed by 1N NaOH (5 mL). The layers were separated and the aq. layer was extracted with CH$_2$Cl$_2$ (2×5 mL). The combined org. extracts were dried over Na$_2$SO$_4$, filtered, and the solvents were removed under reduced pressure to give the title compound as a yellow oil. LC-MS-conditions 07: t$_R$=0.50 min; [M+H]$^+$=225.93.

2-(2-(Chloromethyl)oxazol-4-yl)propan-2-ol

In a flame dried round-bottomed flask equipped with a magnetic stir bar and under inert atmosphere (N$_2$), a solution of methyl 2-(chloromethyl)oxazole-4-carboxylate (Organic Process Research & Development 2001, 5, 37-44) (13.00 g, 74.04 mmol) in THF (433 mL) was treated dropwise at 0° C. with methylmagnesium chloride (51.8 mL of a 3.0 M solution in THF, 155.49 mmol) and the resulting orange solution was stirred for 1.5 h at 0° C. The reaction mixture was carefully poured over an ice-chilled sat. aq. NH$_4$Cl solution (300 mL). It was extracted with EA (3×200 mL) and the combined org. layers were washed with brine (300 mL), dried over MgSO$_4$, filtered and the solvent was removed under reduced pressure. Purification of the residue by FC (6:4 hept-EA) gave the title compound as a yellow oil: TLC: rf (6:4 hept-EA)=0.24. LC-MS-conditions 06: t$_R$=0.49 min.

2-(Chloromethyl)-4-(2-methoxypropan-2-yl)oxazole

In a flame dried round-bottomed flask equipped with a magnetic stir bar and under inert atmosphere (N$_2$), a solution of 2-(2-(chloromethyl)oxazol-4-yl)propan-2-ol (200 mg, 1.14 mmol) in MeI (3.5 mL) was treated with Ag$_2$O (396 mg, 1.71 mmol) and the resulting mixture (protected from light) was stirred for 26 h at 40° C. The reaction mixture was filtered and the MeI was removed under reduced pressure. Purification of the residue by FC (7:3 hept-EA) gave the title compound as a colorless oil: TLC: rf (7:3 hept-EA)=0.33. LC-MS-conditions 06: t$_R$=0.64 min, [M+H]$^+$=190.17.

4-(2-Methoxypropan-2-yl)-2-((4-nitro-2H-1,2,3-triazol-2-yl)methyl)oxazole

In a flame dried round-bottomed flask equipped with a magnetic stir bar and under inert atmosphere (N$_2$), a solution of 2-(chloromethyl)-4-(2-methoxypropan-2-yl)oxazole (134 mg, 0.71 mmol) in DMF (2.0 mL) was added to a solution of 4-nitro-2H-[1,2,3]triazole (T. E. Eagles et al. *Organic prepa-* rations and procedures 2 (2), 117-119, 1970; P. N. Neuman *J. Heterocycl. Chem.* 8, 51-56, 1971) (1.01 g of a 8% solution in DMF, 0.71 mmol) in DMF (2.0 mL) pre-treated for 30 min with DIPEA (0.24 mL, 1.41 mmol) and the reaction mixture was stirred overnight at 50° C. Water (16 mL), followed by EA (16 mL) was added. The layers were separated and the org. layer was washed with water (3×6 mL), dried over MgSO$_4$, filtered, and the solvents were removed under reduced pressure. Purification of the residue by FC (1:1 hept-EA) gave the title compound as a yellow oil: TLC: rf (1:1 hept-EA)=0.33. LC-MS-conditions 06: t$_R$=0.69 min, [M+H]$^+$= 268.13.

2-((4-(2-Methoxypropan-2-yl)oxazol-2-yl)methyl)-2H-1,2,3-triazol-4-amine

In a flame dried round-bottomed flask equipped with a magnetic stir bar and under inert atmosphere (N$_2$), a mixture of 4-(2-methoxypropan-2-yl)-2-((4-nitro-2H-1,2,3-triazol-2-yl)methyl)oxazole (56 mg, 0.21 mmol), iron powder (35 mg, 0.63 mmol) and NH$_4$Cl (57 mg, 1.05 mmol) in a mixture of EtOH (1.0 mL) and water (0.5 mL) was stirred at 85° C. for 15 min. The reaction mixture was filtered while hot and concentrated under reduced pressure. CH$_2$Cl$_2$ (2 mL) was added followed by 1N NaOH (2 mL). The layers were separated and the aq. layer was extracted with CH$_2$Cl$_2$ (2 mL). The combined org. extracts were dried over MgSO$_4$, filtered, and the solvents were removed under reduced pressure to give the title compound as a yellow oil. LC-MS-conditions 06: t$_R$=0.46 min; [M+H]$^+$=238.09.

(2-(Chloromethyl)oxazol-4-yl)methanol

In a flame dried round-bottomed flask equipped with a magnetic stir bar and under inert atmosphere (N$_2$), a solution of methyl 2-(chloromethyl)oxazole-4-carboxylate (Organic Process Research & Development 2001, 5, 37-44) (12.50 g, 71.20 mmol) in THF (400 mL) was treated dropwise at 0° C. with DiBAL-H (242 mL of a 1.0 M solution in THF, 242.0 mmol) and the resulting solution was stirred for 1 h at 0° C. and then allowed to warm to rt. The reaction mixture was carefully poured over a Rochelle's salt solution (600 mL) and EA (250 mL) was added. The mixture was stirred for 1.5 h. The aq. layer was extracted with EA (2×250 mL) and the combined org. layers were dried over MgSO$_4$, filtered and the solvent was removed under reduced pressure. Purification of the residue by FC (1:4 hept-EA) gave the title compound as a yellow oil: TLC: rf (1:4 hept-EA)=0.28. LC-MS-conditions 07: t$_R$=0.39 min; [M+H]$^+$=147.98.

2-(Chloromethyl)-4-(methoxymethyl)oxazole

In a flame dried round-bottomed flask equipped with a magnetic stir bar and under inert atmosphere (N$_2$), a solution of (2-(chloromethyl)oxazol-4-yl)methanol (8.00 g, 54.22 mmol) in CH$_2$Cl$_2$ (32.0 mL) was treated with MeI (4.05 mL, 65.06 mmol) followed by Ag$_2$O (18.85 g, 81.32 mmol) and the resulting mixture (protected from light) was stirred overnight at 40° C. The reaction mixture was filtered and the solvent was removed under reduced pressure. Purification of the residue by FC (6:4 hept-EA) gave the title compound as a yellow oil: TLC: rf (6:4 hept-EA)=0.31. LC-MS-conditions 07: t$_R$=0.54 min, [M+H]$^+$=162.00.

4-(Methoxymethyl)-2-((4-nitro-2H-1,2,3-triazol-2-yl)methyl)oxazole

In a flame dried round-bottomed flask equipped with a magnetic stir bar and under inert atmosphere (N$_2$), a solution of 2-(chloromethyl)-4-(methoxymethyl)oxazole (1.38 g, 8.55 mmol) in DMF (24.0 mL) was added to a solution of 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) (10.16 g of a 9.6% solution in DMF, 8.55 mmol) in DMF (24.0 mL) pre-treated for 30 min with DIPEA (2.93 mL, 17.10 mmol) and the reaction mixture was stirred overnight at 50° C. Water (200 mL), followed by EA (200 mL) was added. The layers were separated and the org. layer was washed with water (3×70 mL), dried over MgSO$_4$, filtered, and the solvents were removed under reduced pressure. Purification of the residue by FC (4:6 hept-EA) gave the title compound as a yellow oil: TLC: rf (4:6 hept-EA)=0.38. LC-MS-conditions 07: t$_R$=0.63 min.

2-((4-(Methoxymethyl)oxazol-2-yl)methyl)-2H-1,2,3-triazol-4-amine

In a flame dried round-bottomed flask equipped with a magnetic stir bar and under inert atmosphere (N$_2$), a mixture of 4-(methoxymethyl)-2-((4-nitro-2H-1,2,3-triazol-2-yl)methyl)oxazole (1.46 g, 6.10 mmol), iron powder (1.03 g, 18.31 mmol) and NH$_4$Cl (1.65 g, 30.52 mmol) in a mixture of EtOH (30.0 mL) and water (15.0 mL) was stirred at 85° C. for 15 min. The reaction mixture was filtered while hot and concentrated under reduced pressure. CH$_2$Cl$_2$ (55 mL) was added followed by 1N NaOH (33 mL). The layers were separated and the aq. layer was extracted with CH$_2$Cl$_2$ (5×50 mL). The combined org. extracts were dried over MgSO$_4$, filtered, and the solvents were removed under reduced pressure to give the title compound as a yellow oil. LC-MS-conditions 07: t$_R$=0.42 min; [M+H]$^+$=210.09.

Methyl 2-(acetoxymethyl)oxazole-4-carboxylate

In a flame dried round-bottomed flask equipped with a magnetic stir bar and under inert atmosphere (N$_2$), a solution of methyl 2-(chloromethyl)oxazole-4-carboxylate (Organic Process Research & Development 2001, 5, 37-44) (20.00 g, 113.91 mmol) in acetic acid (80 mL) was treated with acetic anhydride (8.0 mL) followed by sodium acetate (39.72 g, 484.14 mmol). The reaction mixture was stirred at 120° C. for 3 h. EA (400 mL) was added at rt and the suspension was neutralized with sat. aq. sodium carbonate. The layers were separated and the aq. layer was extracted with EA (2×400 mL). The combined org. layers were dried over Na$_2$SO$_4$, filtered, and the solvents were removed under reduced pressure to give the title compound as a white solid. LC-MS-conditions 06: t$_R$=0.48 min, [M+H]$^+$=200.41.

Methyl 2-(hydroxymethyl)oxazole-4-carboxylate

In a flame dried round-bottomed flask equipped with a magnetic stir bar and under inert atmosphere (N$_2$), sodium (1.32 g, 57.42 mmol) was added portionwise to MeOH (145 mL). Methyl 2-(acetoxymethyl)oxazole-4-carboxylate (23.30 g, 116.99 mmol) was then added and the reaction mixture was stirred for 1 h at rt. Sat. aq. NH$_4$Cl (760 mL) was then added and the mixture was extracted with EA (2×760 mL). The combined org. layers were dried over MgSO$_4$, filtered, and the solvents were removed under reduced pressure to give the title compound as a white solid: TLC: rf (1:9 hept-EA)=0.33. LC-MS-conditions 06: t$_R$=0.31 min, [M+H]$^+$= 158.15.

Methyl 2-(methoxymethyl)oxazole-4-carboxylate

In a flame dried round-bottomed flask equipped with a magnetic stir bar and under inert atmosphere (N$_2$), a solution of methyl 2-(hydroxymethyl)oxazole-4-carboxylate (231 mg, 1.47 mmol) in CH$_2$Cl$_2$ (0.9 mL) was treated with MeI (0.11 mL, 1.76 mmol) followed by Ag$_2$O (511 mg, 2.21 mmol) and the resulting mixture (protected from light) was stirred overnight at 40° C. The reaction mixture was filtered and the solvent was removed under reduced pressure. Purification of the residue by FC (1:1 hept-EA) gave the title compound as a colorless oil: TLC: rf (1:1 hept-EA)=0.33. LC-MS-conditions 07: $t_R$=0.49 min, [M+H]$^+$=172.20.

(2-(Methoxymethyl)oxazol-4-yl)methanol

In a flame dried round-bottomed flask equipped with a magnetic stir bar and under inert atmosphere (N$_2$), a solution of methyl 2-(methoxymethyl)oxazole-4-carboxylate (192 mg, 1.12 mmol) in THF (11 mL) was treated dropwise at 0° C. with LiAlH$_4$ (1.35 mL of a 1.0 M solution in THF, 1.35 mmol) and the resulting solution was stirred for 20 min at 0° C. The reaction mixture was carefully treated with water (1.0 mL) 1N NaOH (1.0 mL) followed by water (1.0 mL) and the mixture was stirred for 1 h at rt. The resulting suspension was filtered, extracted with EA and the combined org. layers were dried over MgSO$_4$, filtered and the solvent was removed under reduced pressure to give the title compound as a brown oil. LC-MS-conditions 07: $t_R$=0.33 min; [M+H]$^+$=144.08.

2-(Methoxymethyl)-4-((4-nitro-2H-1,2,3-triazol-2-yl)methyl)oxazole

In a flame dried round-bottomed flask equipped with a magnetic stir bar and under inert atmosphere (N$_2$), a solution of (2-(methoxymethyl)oxazol-4-yl)methanol (76 mg, 0.53 mmol) in dry CH$_2$Cl$_2$ (5 mL) was treated at 0° C. with Et$_3$N (0.10 mL, 0.69 mmol) followed by DMAP (6.6 mg, 0.05 mmol) and Ms-Cl (0.05 mL, 0.67 mmol). After stirring at 0° C. for 30 min, the reaction was quenched with water (5 mL). The org. layer was dried over Na$_2$SO$_4$, filtered, and the solvents were removed under reduced pressure to give 118 mg of crude (2-(methoxymethyl)oxazol-4-yl)methyl methanesulfonate as a brown oil. LC-MS-conditions 07: $t_R$=0.51 min, [M+H]$^+$=222.02. A solution of this crude material (118 mg) in DMF (1.3 mL) was added to a solution of 4-nitro-2H-[1,2,3]triazole (635 mg of a 9.6% solution in DMF, 0.53 mmol) in DMF (1.3 mL) pre-treated for 30 min with DIPEA (0.18 mL, 1.07 mmol) and the reaction mixture was stirred for 24 h at 50° C. Water (10 mL), followed by EA (10 mL) was added. The aq. layer was extracted with EA (10 mL) and the combined org. extracts were dried over MgSO$_4$, filtered, and the solvents were removed under reduced pressure. Purification of the residue by FC (1:1 hept-EA) gave the title compound as a yellow oil: TLC: rf (1:1 hept-EA)=0.31. LC-MS-conditions 07: $t_R$=0.62 min, [M+H]$^+$=240.10.

2-((2-(Methoxymethyl)oxazol-4-yl)methyl)-2H-1,2,3-triazol-4-amine

In a flame dried round-bottomed flask equipped with a magnetic stir bar and under inert atmosphere (N$_2$), a mixture of 2-(methoxymethyl)-4-((4-nitro-2H-1,2,3-triazol-2-yl)methyl)oxazole (21 mg, 0.09 mmol), iron powder (15 mg, 0.26 mmol) and NH$_4$Cl (24 mg, 0.44 mmol) in a mixture of EtOH (1.0 mL) and water (0.5 mL) was stirred at 85° C. for 15 min. The reaction mixture was filtered while hot and concentrated under reduced pressure. CH$_2$Cl$_2$ (5 mL) was added followed by 1N NaOH (5 mL). The layers were separated and the aq. layer was extracted with CH$_2$Cl$_2$ (2×5 mL). The combined org. extracts were dried over Na$_2$SO$_4$, filtered, and the solvents were removed under reduced pressure to give the title compound as a yellow oil. LC-MS-conditions 07: $t_R$=0.41 min; [M+H]$^+$=210.22.

2-(Chloromethyl)-4-(ethoxymethyl)oxazole

In a flame dried round-bottomed flask equipped with a magnetic stir bar and under inert atmosphere (N$_2$), a solution of (2-(chloromethyl)oxazol-4-yl)methanol (500 mg, 3.39 mmol) in CH$_2$Cl$_2$ (2.0 mL) was treated with EtI (0.28 mL, 3.39 mmol) followed by Ag$_2$O (1.18 g, 5.08 mmol) and the resulting mixture (protected from light) was stirred overnight at 40° C. The reaction mixture was filtered and the solvent was removed under reduced pressure. Purification of the residue by FC (7:3 hept-EA) gave the title compound as a yellow oil: TLC: rf (7:3 hept-EA)=0.29. LC-MS-conditions 07: $t_R$=0.62 min, [M+H]$^+$=176.26.

4-(Ethoxymethyl)-2-((4-nitro-2H-1,2,3-triazol-2-yl)methyl)oxazole

In a flame dried round-bottomed flask equipped with a magnetic stir bar and under inert atmosphere (N$_2$), a solution of 2-(chloromethyl)-4-(ethoxymethyl)oxazole (260 mg, 1.48 mmol) in DMF (4.2 mL) was added to a solution of 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) (1.76 g of a 9.6% solution in DMF, 1.48 mmol) in DMF (4.2 mL) pre-treated for 30 min with DIPEA (0.51 mL, 2.96 mmol) and the reaction mixture was stirred overnight at 50° C. Water (20 mL), followed by EA (20 mL) was added. The layers were separated and the org. layer was washed with water (3×10 mL), dried over MgSO$_4$, filtered, and the solvents were removed under reduced pressure. Purification of the residue by FC (1:1 hept-EA) gave the title compound as a yellow oil: TLC: rf (1:1 hept-EA)=0.40. LC-MS-conditions 07: $t_R$=0.69 min, [M+H]$^+$=254.06.

2-((4-(Ethoxymethyl)oxazol-2-yl)methyl)-2H-1,2,3-triazol-4-amine

In a flame dried round-bottomed flask equipped with a magnetic stir bar and under inert atmosphere (N$_2$), a mixture of 4-(ethoxymethyl)-2-((4-nitro-2H-1,2,3-triazol-2-yl)methyl)oxazole (115 mg, 0.45 mmol), iron powder (77 mg, 1.36 mmol) and NH$_4$Cl (123 mg, 2.27 mmol) in a mixture of EtOH (2.4 mL) and water (1.2 mL) was stirred at 85° C. for 15 min. The reaction mixture was filtered while hot and concentrated under reduced pressure. CH$_2$Cl$_2$ (25 mL) was added followed by 1N NaOH (25 mL). The layers were separated and the aq. layer was extracted with CH$_2$Cl$_2$ (5×25 mL). The combined org. extracts were dried over MgSO$_4$, filtered, and the solvents were removed under reduced pressure to give the title compound as a yellow oil. LC-MS-conditions 07: $t_R$=0.48 min; [M+H]$^+$=224.09.

Preparation of Examples

Example 1

N-(2-((4-(2-Methoxypropan-2-yl)oxazol-2-yl)methyl)-2H-1,2,3-triazol-4-yl)-2-methyl-5-(m-tolyl)oxazole-4-carboxamide In a flame dried round-bottomed flask equipped with a magnetic stir bar and under inert atmosphere (N$_2$), a solution of 2-methyl-5-(m-tolyl)oxazole-4-carboxylic acid (WO 2009/077990, p. 112) (40.0 mg, 0.18 mmol) in $CH_2Cl_2$ (1.0 mL) was treated at rt with DMAP (5.6 mg, 0.05 mmol), HOBt (29.9 mg, 0.22 mmol), EDC (88.3 mg, 0.46 mmol) and DIPEA (0.13 mL, 0.74 mmol) and the resulting mixture was stirred for 45 min at rt. A solution of 2-((4-(2-methoxypropan-2-yl)oxazol-2-yl)methyl)-2H-1,2,3-triazol-4-amine (43.7 mg, 0.18 mmol) in $CH_2Cl_2$ (0.8 mL) was then added and the reaction mixture was stirred overnight at rt. The mixture was diluted with $CH_2Cl_2$ (2.0 mL), the layers were separated and the org. phase was washed with water (2.0 mL), dried over $MgSO_4$, filtered and the solvents were removed under reduced pressure. Purification of the residue by FC (4:6 hept-EA) gave the title compound as a colorless oil: TLC: rf (4:6 hept-EA)=0.35. LC-MS-conditions 06: $t_R$=0.94 min, $[M+H]^+$= 437.34.

Example 2

N-(2-((4-(Methoxymethyl)oxazol-2-yl)methyl)-2H-1,2,3-triazol-4-yl)-2-methyl-5-(m-tolyl)oxazole-4-carboxamide In a flame dried round-bottomed flask equipped with a magnetic stir bar and under inert atmosphere ($N_2$), a solution of 2-methyl-5-(m-tolyl)oxazole-4-carboxylic acid (WO 2009/077990, p. 112) (1.14 g, 5.26 mmol) in $CH_2Cl_2$ (30 mL) was treated at rt with DMAP (160 mg, 1.31 mmol), HOBt (854 mg, 6.32 mmol), EDC (2.52 g, 13.15 mmol) and DIPEA (3.60 mL, 21.03 mmol) and the resulting mixture was stirred for 45 min at rt. A solution of 2-((4-(methoxymethyl)oxazol-2-yl)methyl)-2H-1,2,3-triazol-4-amine (1.10 g, 5.26 mmol) in $CH_2Cl_2$ (22 mL) was then added and the reaction mixture was stirred overnight at rt. The mixture was diluted with $CH_2Cl_2$ (45 mL), the layers were separated and the org. phase was washed with water (45 mL), dried over $MgSO_4$, filtered and the solvents were removed under reduced pressure. Purification of the residue by FC (4:6 hept-EA) gave the title compound as a colorless oil: TLC: rf (4:6 hept-EA)=0.20. LC-MS-conditions 07: $t_R$=0.88 min, $[M+H]^+$=409.11.

Example 3

N-(2-((4-(Methoxymethyl)oxazol-2-yl)methyl)-2H-1,2,3-triazol-4-yl)-2-methyl-5-phenyloxazole-4-carboxamide In a flame dried round-bottomed flask equipped with a magnetic stir bar and under inert atmosphere ($N_2$), a solution of 2-methyl-5-phenyloxazole-4-carboxylic acid (WO 2009/077990, p. 113) (955 mg, 4.70 mmol) in $CH_2Cl_2$ (27 mL) was treated at rt with DMAP (143 mg, 1.17 mmol), HOBt (763 mg, 5.65 mmol), EDC (2.25 g, 11.75 mmol) and DIPEA (3.22 mL, 18.80 mmol) and the resulting mixture was stirred for 45 min at rt. A solution of 2-((4-(methoxymethyl)oxazol-2-yl)methyl)-2H-1,2,3-triazol-4-amine (983 mg, 4.70 mmol) in $CH_2Cl_2$ (20 mL) was then added and the reaction mixture was stirred overnight at rt. The mixture was diluted with $CH_2Cl_2$ (40 mL), the layers were separated and the org. phase was washed with water (40 mL), dried over $MgSO_4$, filtered and the solvents were removed under reduced pressure. Purification of the residue by crystallization for EA to give the title compound as a white solid: TLC: rf (4:6 hept-EA)=0.14. LC-MS-conditions 07: $t_R$=0.84 min, $[M+H]^+$=395.44.

Example 4

5-(3-Chlorophenyl)-N-(2-((4-(methoxymethyl)oxazol-2-yl)methyl)-2H-1,2,3-triazol-4-yl)-2-methyloxazole-4-carboxamide Synthesized according to GP1 using 5-(3-chlorophenyl)-2-methyl-oxazole-4-carboxylic acid (WO 2009/077990, page 113). LC-MS-conditions 10: $t_R$=1.14 min, $[M+H]^+$=429.05.

Example 5

N-(2-((4-(Methoxymethyl)oxazol-2-yl)methyl)-2H-1,2,3-triazol-4-yl)-2-methyl-5-(3-(trifluoromethyl)phenyl)oxazole-4-carboxamide Synthesized according to GP1 using 2-methyl-5-(3-(trifluoromethyl)phenyl)oxazole-4-carboxylic acid (WO 2009/077990, page 113). LC-MS-conditions 10: $t_R$=1.18 min, $[M+H]^+$=463.03.

Example 6

5-(3-Chlorophenyl)-N-(2-((4-(methoxymethyl)oxazol-2-yl)methyl)-2H-1,2,3-triazol-4-yl)oxazole-4-carboxamide Synthesized according to GP1 using 5-(3-chlorophenyl)oxazole-4-carboxylic acid (WO 2009/077990, page 114). LC-MS-conditions 10: $t_R$=1.03 min, $[M+H]^+$=415.02.

Example 7

N-(2-((4-(Methoxymethyl)oxazol-2-yl)methyl)-2H-1,2,3-triazol-4-yl)-5-(3-methoxyphenyl)oxazole-4-carboxamide Synthesized according to GP1 using 5-(3-methoxyphenyl)oxazole-4-carboxylic acid (WO 2009/077990, page 114). LC-MS-conditions 10: $t_R$=0.92 min, $[M+H]^+$=411.09.

Example 8

N-(2-((4-(Methoxymethyl)oxazol-2-yl)methyl)-2H-1,2,3-triazol-4-yl)-5-(3-methoxyphenyl)-2-methyloxazole-4-carboxamide Synthesized according to GP1 using 5-(3-methoxyphenyl)-2-methyl-oxazole-4-carboxylic acid (WO 2009/077990, page 112). LC-MS-conditions 10: $t_R$=1.02 min, $[M+H]^+$=425.08.

Example 9

5-(3-Fluorophenyl)-N-(2-((4-(methoxymethyl)oxazol-2-yl)methyl)-2H-1,2,3-triazol-4-yl)-2-methyloxazole-4-carboxamide Synthesized according to GP1 using 5-(3-fluorophenyl)-2-methyloxazole-4-carboxylic acid (WO 2009/077990, page 112). LC-MS-conditions 10: $t_R$=1.04 min, $[M+H]^+$=413.07.

Example 10

N-(2-((4-(Methoxymethyl)oxazol-2-yl)methyl)-2H-1,2,3-triazol-4-yl)-5-(m-tolyl)oxazole-4-carboxamide Synthesized according to GP1 using 5-(m-tolyl)oxazole-4-carboxylic acid (WO 2009/077990, page 114). LC-MS-conditions 10: $t_R$=1.00 min, $[M+H]^+$=395.12.

Example 11

N-(2-((4-(Methoxymethyl)oxazol-2-yl)methyl)-2H-1,2,3-triazol-4-yl)-2-methyl-5-(3-(trifluoromethoxy)phenyl)oxazole-4-carboxamide Synthesized according to GP1 using 2-methyl-5-(3-(trifluoromethoxy)phenyl)oxazole-4-carboxylic acid (WO 2009/077990, page 113). LC-MS-conditions 10: $t_R$=1.22 min, $[M+H]^+$=479.05.

Example 12

2-Cyclopropyl-N-(2-((4-(methoxymethyl)oxazol-2-yl)methyl)-2H-1,2,3-triazol-4-yl)-5-(m-tolyl)oxazole-4-carboxamide Synthesized according to GP1 using 2-cyclopropyl-5-(m-tolyl)oxazole-4-carboxylic acid (prepared as for 2-cyclopropyl-5-phenyl-oxazole-4-carboxylic acid in WO 2009/077990, page 114, but starting from ethyl 3-oxo-3-(m-tolyl)propanoate). LC-MS-conditions 10: $t_R$=1.25 min, $[M+H]^+$=435.09.

Example 13

N-(2-((4-(Methoxymethyl)oxazol-2-yl)methyl)-2H-1,2,3-triazol-4-yl)-5-phenyloxazole-4-carboxamide In a flame dried round-bottomed flask equipped with a magnetic stir bar and under inert atmosphere ($N_2$), a solution of commercially available 5-phenyloxazole-4-carboxylic acid (50 mg, 0.26 mmol) in $CH_2Cl_2$ (1.3 mL) was treated at rt with DMAP (8 mg, 0.07 mmol), HOBt (43 mg, 0.32 mmol), EDC (127 mg, 0.67 mmol) and DIPEA (0.18 mL, 1.06 mmol) and the resulting mixture was stirred for 45 min at rt. A solution of 2-((4-(methoxymethyl)oxazol-2-yl)methyl)-2H-1,2,3-triazol-4-amine (55 mg, 0.26 mmol) in $CH_2Cl_2$ (1.3 mL) was then added and the reaction mixture was stirred overnight at rt. The mixture was diluted with $CH_2Cl_2$ (5 mL), the layers were separated and the org. phase was washed with water (5 mL), dried over $Na_2SO_4$, filtered and the solvents were removed under reduced pressure. Purification of the residue by FC (4:6 hept-EA) gave the title compound as a white solid: TLC: rf (4:6 hept-EA)=0.13. LC-MS-conditions 07: $t_R$=0.81 min, $[M+H]^+$=381.14.

Example 14

N-(2-((4-(ethoxymethyl)oxazol-2-yl)methyl)-2H-1,2,3-triazol-4-yl)-2-methyl-5-(m-tolyl)oxazole-4-carboxamide In a flame dried round-bottomed flask equipped with a magnetic stir bar and under inert atmosphere ($N_2$), a solution of 2-methyl-5-(m-tolyl)oxazole-4-carboxylic acid (WO 2009/077990, p. 112) (42 mg, 0.20 mmol) in $CH_2Cl_2$ (1.0 mL) was treated at rt with DMAP (5.8 mg, 0.05 mmol), HOBt (31 mg, 0.23 mmol), EDC (91 mg, 0.48 mmol) and DIPEA (0.13 mL, 0.76 mmol) and the resulting mixture was stirred for 45 min at rt. A solution of 2-((4-(ethoxymethyl)oxazol-2-yl)methyl)-2H-1,2,3-triazol-4-amine (43 mg, 0.19 mmol) in $CH_2Cl_2$ (0.9 mL) was then added and the reaction mixture was stirred overnight at rt. The mixture was diluted with $CH_2Cl_2$ (10 mL) and the org. phase was washed with water (10 mL), dried over $MgSO_4$, filtered and the solvents were removed under reduced pressure. Purification of the residue by FC (3:7 hept-EA) gave the title compound as a yellow oil: TLC: rf (7:3 hept-EA)=0.34. LC-MS-conditions 07: $t_R$=0.91 min, $[M+H]^+$=423.14.

Example 15

N-(2-((4-(ethoxymethyl)oxazol-2-yl)methyl)-2H-1,2,3-triazol-4-yl)-5-phenyloxazole-4-carboxamide In a flame dried round-bottomed flask equipped with a magnetic stir bar and under inert atmosphere ($N_2$), a solution of commercially available 5-phenyloxazole-4-carboxylic acid (36 mg, 0.19 mmol) in $CH_2Cl_2$ (1.0 mL) was treated at rt with DMAP (5.8 mg, 0.05 mmol), HOBt (31 mg, 0.23 mmol), EDC (91 mg, 0.48 mmol) and DIPEA (0.13 mL, 0.76 mmol) and the resulting mixture was stirred for 45 min at rt. A solution of 2-((4-(ethoxymethyl)oxazol-2-yl)methyl)-2H-1,2,3-triazol-4-amine (43 mg, 0.19 mmol) in $CH_2Cl_2$ (0.9 mL) was then added and the reaction mixture was stirred overnight at rt. The mixture was diluted with $CH_2Cl_2$ (10 mL) and the org. phase was washed with water (10 mL), dried over $MgSO_4$, filtered and the solvents were removed under reduced pressure. Purification of the residue by FC (3:7 hept-EA) gave the title compound as a yellow oil: TLC: rf (7:3 hept-EA)=0.34. LC-MS-conditions 07: $t_R$=0.84 min, $[M+H]^+$=395.08.

II. Biological Assays

In Vitro Assay

The ALX receptor agonistic activity of the compounds of formula (I) is determined in accordance with the following experimental method.

Experimental Method:

Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1,000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% $CO_2$ in AB supplemented with 1 μM Fluo-4 (AM) (Invitrogen, F14202) and 20 mM HEPES (Gibco, 15630-056), the cells were washed and resuspended in AB. They were then seeded onto 384-well FLIPR assay plates (Greiner, 781091) at 50,000 cells in 70 μl per well and sedimented by centrifugation at 1,000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR Tetra instrument (Molecular Devices) was operated according to the manufacturer's standard instructions, adding 4 μl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Agonistic activities with respect to the ALX receptor ($EC_{50}$ values) of exemplified compounds are displayed in Table 1.

TABLE 1

| Compound | $EC_{50}$ [nM] |
|---|---|
| Example 1: N-(2-((4-(2-methoxypropan-2-yl)oxazol-2-yl)methyl)-2H-1,2,3-triazol-4-yl)-2-methyl-5-(m-tolyl)oxazole-4-carboxamide | 6.6 |
| Example 2: N-(2-((4-(methoxymethyl)oxazol-2-yl)methyl)-2H-1,2,3-triazol-4-yl)-2-methyl-5-(m-tolyl)oxazole-4-carboxamide | 1.7 |
| Example 3: N-(2-((4-(methoxymethyl)oxazol-2-yl)methyl)-2H-1,2,3-triazol-4-yl)-2-methyl-5-phenyloxazole-4-carboxamide | 4.3 |
| Example 4: 5-(3-chlorophenyl)-N-(2-((4-(methoxymethyl)oxazol-2-yl)methyl)-2H-1,2,3-triazol-4-yl)-2-methyloxazole-4-carboxamide | 2.1 |
| Example 5: N-(2-((4-(methoxymethyl)oxazol-2-yl)methyl)-2H-1,2,3-triazol-4-yl)-2-methyl-5-(3-(trifluoromethyl)phenyl)oxazole-4-carboxamide | 5.6 |
| Example 6: 5-(3-chlorophenyl)-N-(2-((4-(methoxymethyl)oxazol-2-yl)methyl)-2H-1,2,3-triazol-4-yl)oxazole-4-carboxamide | 4.0 |
| Example 7: N-(2-((4-(methoxymethyl)oxazol-2-yl)methyl)-2H-1,2,3-triazol-4-yl)-5-(3-methoxyphenyl)oxazole-4-carboxamide | 17.5 |
| Example 8: N-(2-((4-(methoxymethyl)oxazol-2-yl)methyl)-2H-1,2,3-triazol-4-yl)-5-(3-methoxyphenyl)-2-methyloxazole-4-carboxamide | 8.8 |
| Example 9: 5-(3-fluorophenyl)-N-(2-((4-(methoxymethyl)oxazol-2-yl)methyl)-2H-1,2,3-triazol-4-yl)-2-methyloxazole-4-carboxamide | 3.7 |
| Example 10: N-(2-((4-(methoxymethyl)oxazol-2-yl)methyl)-2H-1,2,3-triazol-4-yl)-5-(m-tolyl)oxazole-4-carboxamide | 4.6 |
| Example 11: N-(2-((4-(methoxymethyl)oxazol-2-yl)methyl)-2H-1,2,3-triazol-4-yl)-2-methyl-5-(3-(trifluoromethoxy)phenyl)oxazole-4-carboxamide | 7.4 |
| Example 12: 2-cyclopropyl-N-(2-((4-(methoxymethyl)oxazol-2-yl)methyl)-2H-1,2,3-triazol-4-yl)-5-(m-tolyl)oxazole-4-carboxamide | 11.6 |
| Example 13: N-(2-((4-(methoxymethyl)oxazol-2-yl)methyl)-2H-1,2,3-triazol-4-yl)-5-phenyloxazole-4-carboxamide | 5.0 |
| Example 14: N-(2-((4-(ethoxymethyl)oxazol-2-yl)methyl)-2H-1,2,3-triazol-4-yl)-2-methyl-5-(m-tolyl)oxazole-4-carboxamide | 6.7 |
| Example 15: N-(2-((4-(ethoxymethyl)oxazol-2-yl)methyl)-2H-1,2,3-triazol-4-yl)-5-phenyloxazole-4-carboxamide | 8.6 |

Comparative Test Results

In contrast to compounds disclosed in WO 2009/077990 the kind of the heteroaryl group attached to the alkoxy-alkylether moiety has a surprisingly high influence on the agonistic activity of the present compounds. High agonistic activities are only obtained for heteroaryl groups having a nitrogen atom between the two substituted carbon atoms and especially for oxazol-2,4-diyl groups which are substituted by the alkoxy-alkyl moiety in 4-position. The results presented in table 2 are obtained by intracellular calcium measurements as described above.

TABLE 2

| reference compounds | | | |
|---|---|---|---|
| compound falling within formula I of WO 2009/077990 | EC$_{50}$ [nM] | reference compounds | EC$_{50}$ [nM] |
| example 91 | 0.7 | example 13 | 5.0 |
| example 67 | 73 | (reference compound 1) | 4810 |
| example 73 | 88 | (reference compound 2) | 2540 |

TABLE 2-continued reference compounds

| compound falling within formula I of WO 2009/077990 | EC$_{50}$ [nM] | reference compounds | EC$_{50}$ [nM] |
|---|---|---|---|
| example 1 | 1.8 | (reference compound 3) | 498 |
| example 33 | 2.8 | (reference compound 4) | 2300 |
| example 39 | 8.1 | (reference compound 5) | 48 |

TABLE 2-continued

| compound falling within formula I of WO 2009/077990 | EC$_{50}$ [nM] | reference compounds | EC$_{50}$ [nM] |
|---|---|---|---|
| example 45 | 93 | (reference compound 6) | 146 |
| example 67 | 73 | (reference compound 7) | 8130 |
| example 73 | 88 | (reference compound 8) | 5950 |

TABLE 2-continued reference compounds

| compound falling within formula I of WO 2009/077990 | $EC_{50}$ [nM] | reference compounds | $EC_{50}$ [nM] |
|---|---|---|---|
| [structure] | 1.5 | [structure] (reference compound 9) | 685 |
| [structure] | 0.9 | [structure] (reference compound 10) | 8.1 |

Assay for Covalent Binding Between Reactive Metabolites and Proteins Using Human Liver Microsomes The objective of the described covalent binding assay is to determine the amount of covalent binding between reactive metabolites and proteins of human liver microsomes (HLM) per hour following incubation in the presence of an NADPH regenerating system. The measured covalent binding rate is expressed in pmol bound drug equivalent/mg protein/h. It is a well-known advantage if compounds have a low tendency to bind covalently to proteins.

Incubation

The radiolabelled compounds ($^3$H or $^{14}$C) were incubated at a concentration of 10 µM in a single 96 well plate with 1.0 mg/mL of human liver microsomes in 0.1 M phosphate buffer (pH 7.4). To this end, a volume of 2.5 µL 1 mM stock solution prepared in the respective solvent (ethanol) was added to a final volume of 250 µL. Incubations were performed in the absence or presence of the NADPH-regenerating system with glucose-6-phosphate dehydrogenase (20 IU/ml dehydrogenase, 25 µl with 11 mM NADP sodium salt, 100 mM glucose-6-phosphate disodium salt, 100 mM $MgCl_2$ in 0.1 M Tris buffer, pH 7.4) and additionally in the absence or presence of 5 mM GSH to trap reactive intermediates. An initial blank value without NADPH without incubation was also determined to determine unspecific rapid binding. Reactions were initiated by addition of 25 µL of an NADPH-regenerating system and terminated after one hour by adding 200 µL of the incubation mixture on a multiscreen deep well solvinert 96 hydrophobic PTFE filter plate (Millipore, Zug, Switzerland) containing 260 µL of ice-cold acetonitrile. The precipitation of microsomal proteins was completed by shaking the plate at 600 rpm at a temperature of 15° C. for 15 min. Finally, the precipitated incubation was stored at 4° C. for 15 min in the fridge.

Proteins and filtrates were separated by centrifugation at 1800 g for 20 min at 10° C. The protein pellet was washed to remove unspecific binding with 800 µL of methanol/0.1% sulfuric acid (v/v) by centrifugation at 1500 g, 10° C. and 2 min. The washing step was repeated six times. The washed protein pellet was redissolved by addition of 500 µL of aqueous 0.1% (w/v) NaOH/1% (w/v) SDS. The filter plate was shaken at 400 rpm for 45 min at 60° C. and centrifugated at 2000 g for 20 min at 35° C. This step was repeated once and the protein solutions were combined.

For the determination of total radioactivity, an aliquot of 400 µL protein solution was mixed with 4 mL of liquid scintillation cocktail (Irga Safe plus, Perkin Elmer, Zürich, Switzerland) and analyzed using a Tricarb 2300 TR liquid scintillation analyzer (Perkin Elmer) with luminescence correction and on-line quenching correction by means of an external standard ($^{133}$Ba). For the determination of total protein content, an aliquot of 20 µL protein solution was analyzed using the BCA protein assay kit (Perbio Science Switzerland SA, Lausanne, Switzerland). The amount of covalent binding to microsomal proteins was calculated as follows: Dividing the determined amount of bound drug equivalent with NADPH (background subtracted by the amount of bound drug equivalent without NADPH) by the calculated amount of protein of redissolved washed protein pellet in each well gives the amount of bound drug equivalent in pmol/mg protein per hour.

Plasma Stability Assay

Rat or human plasma adjusted at pH 7.4 with lactic acid or ammonium hydroxide, were equilibrated at 37° C. under orbital shaking in an incubator containing 5% $CO_2$. The reaction was initiated by the addition of 1 μM of compounds (1 μl of 1 mM stock solution in DMSO in 999 μl of plasma). At 0.01 h, 0.25 h, 0.5 h, 1 h, 2 h, 4 h, 6 h and 24 h, aliquots (30 μl) were transferred in a 96 well plate containing 90 μl MeOH placed on ice to stop the reaction. After vortexing for 20 min at 1400 rpm on an Eppendorf thermomixer, the plates were centrifuged at 3220 g for 20 min at 4° C. and the supernatants were analyzed with LC-MSMS. Calibration samples in plasma containing 0.1% of dichlorvos were prepared and analysed in parallel to the incubation samples to allow the quantification. Half lives in hours were then calculated. In addition the remaining concentration of the respective compound after time $T_{last}$ relative to the concentration at the beginning has been determined (table 3).

TABLE 3 stability in plasma

| compound | number of replicates | species | $T_{1/2}$ [h] | $T_{last}$ [h] | remaining concentration at $T_{last}$ [%] |
|---|---|---|---|---|---|
| example 2 | 3 | human | >24 | 24 | 101 |
| example 2 | 3 | rat | >24 | 24 | 88 |
| reference compound 11 | 3 | human | 2.4 | 6 | 18 |
| reference compound 11 | 3 | rat | 4.7 | 6 | 42 |

The data demonstrate that example 2 is remarkably more stable in plasma than reference compound 11.

Plasma Stability Assay with Tritiated Compounds

Rat or human plasma adjusted at pH 7.4 with lactic acid were equilibrated at 37° C. under orbital shaking. The reaction was initiated by the addition of 10 μM of tritiated compound (7.5 μl of 1 mM stock solution in DMSO in 742.5 μl of plasma). At the beginning and after 4 h, 6 h and 24 h, aliquots (100 μl) were transferred in a tube containing 400 μl MeOH placed on ice to stop the reaction. After vortexing for 20 min at 1400 rpm on an Eppendorf thermomixer, the plates were centrifuged at 3220 g for 20 min at 4° C. and an aliquot of supernatants was analyzed with liquid chromatography coupled to a H3-radiodetector. The remaining pellet was further extracted with AcCN in three additional cycles of resuspension, mixing 20 min at 2000 rpm on an eppendorf thermomixer and centrifugation (3220 g for 20 min at 4° C.). The total radioactivity was measured in the collected supernatants. The final pellet was then solubilized in NaOH 1N and the total radioactivity was measured (table 4).

TABLE 4 stability of reference compound 11 in plasma

| | nominal incubation time [h] | | | |
|---|---|---|---|---|
| | 0.01 | 4.0 | 6.4 | 24.4 |
| | total radioactivity [dpm] | | | |
| rat plasma supernatant | 173116 | 94798 | 45228 | 4816 |
| rat plasma pellet | 419 | 124853 | 153683 | 180032 |
| human plasma supernatant | 158854 | 38918 | 10532 | 3134 |
| human plasma pellet | 918 | 170136 | 185420 | 227567 |

After HPLC analysis, only reference compound 11 was detected at the different timepoints in the supernatants of the first cycle of extraction. Reference compound 11 was disappearing from the supernatant while radioactivity was appearing in the collected pellets, which suggest a strong association of drug related material with plasma proteins.

The invention claimed is:
1. A compound of the formula (I),

(I)

wherein
  $R^1$ represents phenyl which is unsubstituted or mono-substituted with halogen, $(C_1-C_4)$alkyl, $(C_1-C_4)$alkoxy, $(C_1-C_2)$fluoroalkyl or $(C_1-C_2)$fluoroalkoxy;
  $R^2$ represents hydrogen, methyl or cyclopropyl;
  $R^3$ and $R^4$ are identical and represent hydrogen or methyl; and
  $R^5$ represents $(C_1-C_2)$alkyl; or a salt thereof.
2. The compound according to claim 1, wherein
  $R^1$ represents phenyl which is unsubstituted or mono-substituted with fluoro, chloro, methyl, methoxy, trifluoromethyl or trifluoromethoxy;
  $R^2$ represents hydrogen or methyl;
  $R^3$ and $R^4$ are identical and represent hydrogen or methyl; and
  $R^5$ represents methyl; or a salt thereof.
3. The compound according to claim 1, wherein
  $R^1$ represents phenyl which is unsubstituted or mono-substituted with fluoro, chloro, methyl, methoxy, trifluoromethyl or trifluoromethoxy; or a salt thereof.
4. The compound according to claim 1, wherein when $R^1$ represents a mono-substituted phenyl group, said phenyl group is substituted in meta-position; or a salt thereof.
5. The compound according to claim 1, wherein $R^2$ represents hydrogen or methyl; or a salt thereof.
6. The compound according to claim 1, wherein $R^2$ represents methyl; or a salt thereof.
7. The compound according to claim 1, wherein $R^3$ and $R^4$ both represent hydrogen; or a salt thereof.
8. The compound according claim 1, wherein $R^3$ and $R^4$ both represent methyl; or a salt thereof.
9. The compound according claim 1, wherein $R^5$ represents methyl; or a salt thereof.
10. The compound according to claim 1, wherein the compound is:
  N-(2-((4-(2-methoxypropan-2-yl)oxazol-2-yl)methyl)-2H-1,2,3-triazol-4-yl)-2-methyl-5-(m-tolyl)oxazole-4-carboxamide;
  N-(2-((4-(methoxymethyl)oxazol-2-yl)methyl)-2H-1,2,3-triazol-4-yl)-2-methyl-5-(m-tolyl)oxazole-4-carboxamide;
  N-(2-((4-(methoxymethyl)oxazol-2-yl)methyl)-2H-1,2,3-triazol-4-yl)-2-methyl-5-phenyloxazole-4-carboxamide;

5-(3-chlorophenyl)-N-(2-((4-(methoxymethyl)oxazol-2-yl)methyl)-2H-1,2,3-triazol-4-yl)-2-methyloxazole-4-carboxamide;

N-(2-((4-(methoxymethyl)oxazol-2-yl)methyl)-2H-1,2,3-triazol-4-yl)-2-methyl-5-(3-(trifluoromethyl)phenyl)oxazole-4-carboxamide;

5-(3-chlorophenyl)-N-(2-((4-(methoxymethyl)oxazol-2-yl)methyl)-2H-1,2,3-triazol-4-yl)oxazole-4-carboxamide;

N-(2-((4-(methoxymethyl)oxazol-2-yl)methyl)-2H-1,2,3-triazol-4-yl)-5-(3-methoxyphenyl)oxazole-4-carboxamide;

N-(2-((4-(methoxymethyl)oxazol-2-yl)methyl)-2H-1,2,3-triazol-4-yl)-5-(3-methoxyphenyl)-2-methyloxazole-4-carboxamide;

5-(3-fluorophenyl)-N-(2-((4-(methoxymethyl)oxazol-2-yl)methyl)-2H-1,2,3-triazol-4-yl)-2-methyloxazole-4-carboxamide;

N-(2-((4-(methoxymethyl)oxazol-2-yl)methyl)-2H-1,2,3-triazol-4-yl)-5-(m-tolyl)oxazole-4-carboxamide;

N-(2-((4-(methoxymethyl)oxazol-2-yl)methyl)-2H-1,2,3-triazol-4-yl)-2-methyl-5-(3-(trifluoromethoxy)phenyl)oxazole-4-carboxamide;

2-cyclopropyl-N-(2-((4-(methoxymethyl)oxazol-2-yl)methyl)-2H-1,2,3-triazol-4-yl)-5-(m-tolyl)oxazole-4-carboxamide; or N-(2-((4-(methoxymethyl)oxazol-2-yl)methyl)-2H-1,2,3-triazol-4-yl)-5-phenyloxazole-4-carboxamide; or a salt thereof.

11. The compound according to claim 1, wherein the compound is:

N-(2-((4-(ethoxymethyl)oxazol-2-yl)methyl)-2H-1,2,3-triazol-4-yl)-2-methyl-5-(m-tolyl)oxazole-4-carboxamide; or N-(2-((4-(ethoxymethyl)oxazol-2-yl)methyl)-2H-1,2,3-triazol-4-yl)-5-phenyloxazole-4-carboxamide; or a salt thereof.

12. A medicament comprising the compound according to claim 1, or a pharmaceutically acceptable salt thereof and a pharmaceutically acceptable excipient.

13. A pharmaceutical composition comprising, as active principle, a compound of formula (I) according to claim 1 or a pharmaceutically acceptable salt thereof, and at least one therapeutically inert excipient.

14. A method of treating a disease or condition comprising administering to a subject in need thereof a therapeutically effective amount of a compound according to claim 1, wherein the disease is inflammation mediated by the lipoxin A4 receptor pathway.

15. A method of treating a disease or condition comprising administering to a subject in need thereof a therapeutically effective amount of the compound according to claim 10, wherein the disease is inflammation mediated by the lipoxin A4 receptor pathway.

16. A method of treating a disease or condition comprising administering to a subject in need thereof a therapeutically effective amount of a compound according to claim 1, wherein the disease is Alzheimer's disease mediated by the lipoxin A4 receptor pathway.

17. A method of treating a disease or condition comprising administering to a subject in need thereof a therapeutically effective amount of the compound according to claim 10, wherein the disease is Alzheimer's disease mediated by the lipoxin A4 receptor pathway.

* * * * *